United States Patent [19]

Buell

[11] Patent Number: 5,300,055

[45] Date of Patent: * Apr. 5, 1994

[54] ABSORBENT ARTICLE HAVING A THERMOPLASTIC DEFORMABLE ELEMENT

[75] Inventor: Kenneth B. Buell, Wyoming, Ohio

[73] Assignee: The Procter & Gamble Company, Cincinnati, Ohio

[*] Notice: The portion of the term of this patent subsequent to Dec. 15, 2009 has been disclaimed.

[21] Appl. No.: 989,276

[22] Filed: Dec. 11, 1992

Related U.S. Application Data

[63] Continuation of Ser. No. 825,456, Jan. 21, 1992, Pat. No. 5,171,302, which is a continuation of Ser. No. 175,817, Mar. 31, 1988, abandoned.

[51] Int. Cl.$^5$ ............................................. A61F 13/16
[52] U.S. Cl. ................................. 604/385.1; 604/385.2
[58] Field of Search ............... 604/358, 369, 370, 378, 604/385.1, 385.2, 400–402

[56] References Cited

U.S. PATENT DOCUMENTS

| | | | |
|---|---|---|---|
| 1,974,578 | 9/1934 | Medoff | 604/374 |
| 1,977,133 | 10/1934 | Linard | 604/385.1 X |
| 2,064,431 | 12/1936 | Jurgensen | 604/385 |
| 2,331,355 | 10/1943 | Strongson | 604/365 |
| 2,662,527 | 12/1953 | Jacks | 128/398 |
| 2,747,575 | 5/1956 | Mercer | 604/385 |
| 2,787,271 | 4/1957 | Clark | 604/379 |
| 3,343,543 | 9/1967 | Glassman | 604/385.1 |
| 3,406,689 | 10/1968 | Hicks et al. | 604/401 |
| 3,411,504 | 11/1968 | Glassman | 604/402 |
| 3,528,422 | 9/1970 | Hodas | 128/290 |
| 3,570,493 | 3/1971 | Olsson | 128/290 |
| 3,575,174 | 4/1971 | Mogor | 128/290 |
| 3,805,790 | 4/1974 | Kaczmarzyk | 128/290 R |

(List continued on next page.)

FOREIGN PATENT DOCUMENTS

| | | |
|---|---|---|
| 32360/84 | 8/1984 | Australia . |
| 4004729 | 8/1990 | Fed. Rep. of Germany . |
| 2168612 | 6/1986 | United Kingdom . |
| 2191098 | 12/1987 | United Kingdom . |
| 88/04547 | 6/1988 | World Int. Prop. O. . |

*Primary Examiner*—Randall L. Green
*Assistant Examiner*—R. Clarke
*Attorney, Agent, or Firm*—Steven W. Miller; Jeffrey V. Bamber; E. Kelly Linman

[57] ABSTRACT

The present invention is directed to a disposable absorbent article, and particularly a sanitary napkin, having a flexure-resistant deformation element, the deformation element having a body facing surface which has a convex upward configuration when the sanitary napkin is worn. Primarily without relying on lateral compressive forces of the wearer's labia, the deformation element of the present invention relies on the lateral compressive forces of the wearer's thighs in order to form or maintain a convex upward configuration when the sanitary napkin is worn. In a preferred embodiment, the deformation element has a flexure means, and particularly a longitudinally extending flexure hinge, for inducing the body facing surface of the deformation element to have a convex upward configuration when the sanitary napkin is worn. In an alternatively preferred embodiment, the deformation element has a central region having a "W" shaped cross-section wherein the body facing surface of the deformation element having the convex upward configuration is located in the central region, generally symmetrically between the longitudinal side edges of the napkin. In another alternatively preferred embodiment, the deformation element has a cup-shaped front region and a back region having a convex upward configured body facing surface. The deformation element may be a moldable substance such as a foam, it may be reformable and/or it may be resilient.

11 Claims, 8 Drawing Sheets

U.S. PATENT DOCUMENTS

| | | | |
|---|---|---|---|
| 4,067,336 | 1/1978 | Johnson | 604/284 |
| 4,182,334 | 1/1980 | Johnson | 128/287 |
| 4,195,634 | 4/1980 | DiSalvo et al. | 604/385 |
| 4,340,058 | 7/1982 | Pierce et al. | 128/287 |
| 4,405,326 | 9/1983 | Lenaghan | 604/385 |
| 4,551,142 | 11/1985 | Kopolow | 604/368 |
| 4,554,191 | 11/1985 | Korpman | 428/35 |
| 4,595,392 | 6/1986 | Johnson et al. | 604/385 R |
| 4,627,848 | 12/1986 | Lassen et al. | 604/370 |
| 4,631,062 | 12/1986 | Lassen et al. | 604/385 R |
| 4,655,759 | 4/1987 | Romans-Hess et al. | 604/385 R |
| 4,666,440 | 5/1987 | Malfitano | 604/391 |
| 4,673,403 | 6/1987 | Lassen et al. | 604/385 R |
| 4,681,577 | 7/1987 | Stern et al. | 604/378 |
| 4,685,914 | 8/1987 | Holtman | 604/368 |
| 4,701,177 | 10/1987 | Ellis et al. | 604/385 A |
| 4,758,240 | 7/1988 | Glassman | 604/379 |
| 4,804,380 | 2/1989 | Lassen et al. | 604/385 |
| 4,865,597 | 9/1989 | Mason et al. | 604/385.1 |
| 4,886,513 | 12/1989 | Mason et al. | 604/385.1 |
| 5,098,422 | 3/1992 | Davis et al. | 604/385.1 |

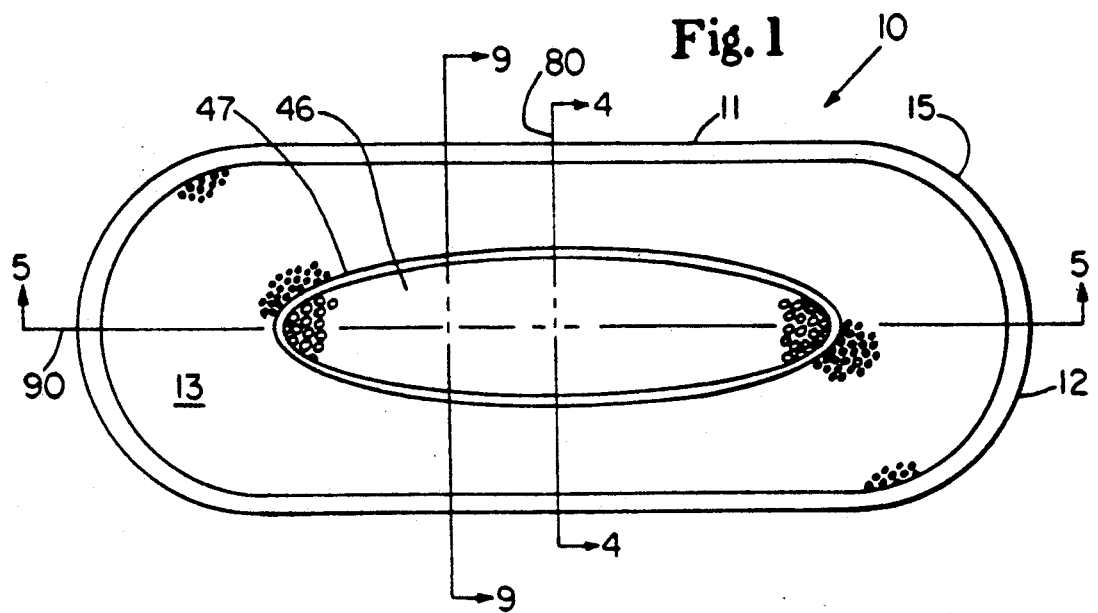
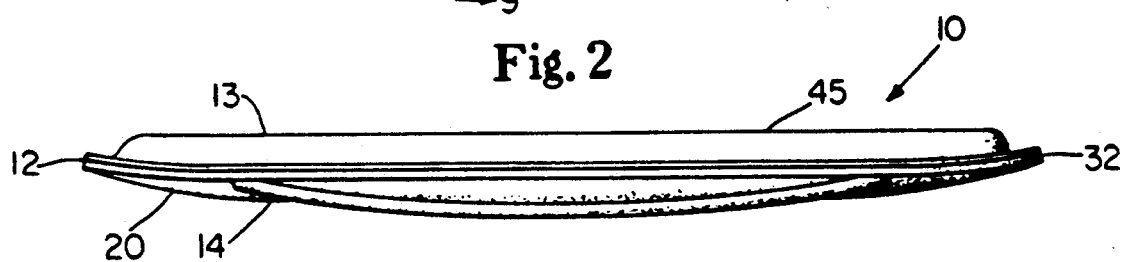
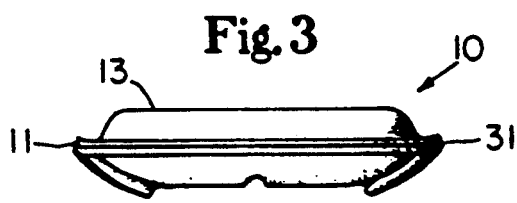
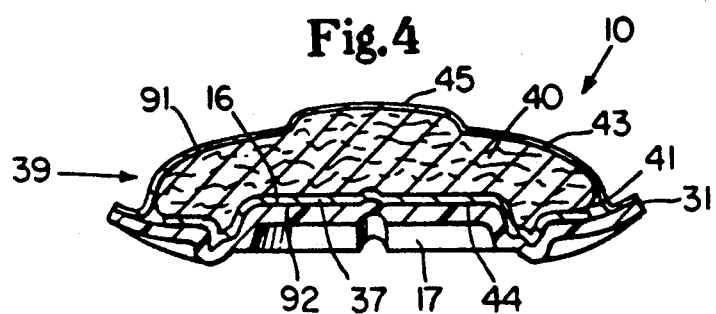

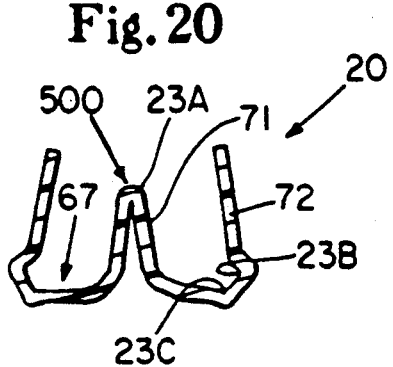
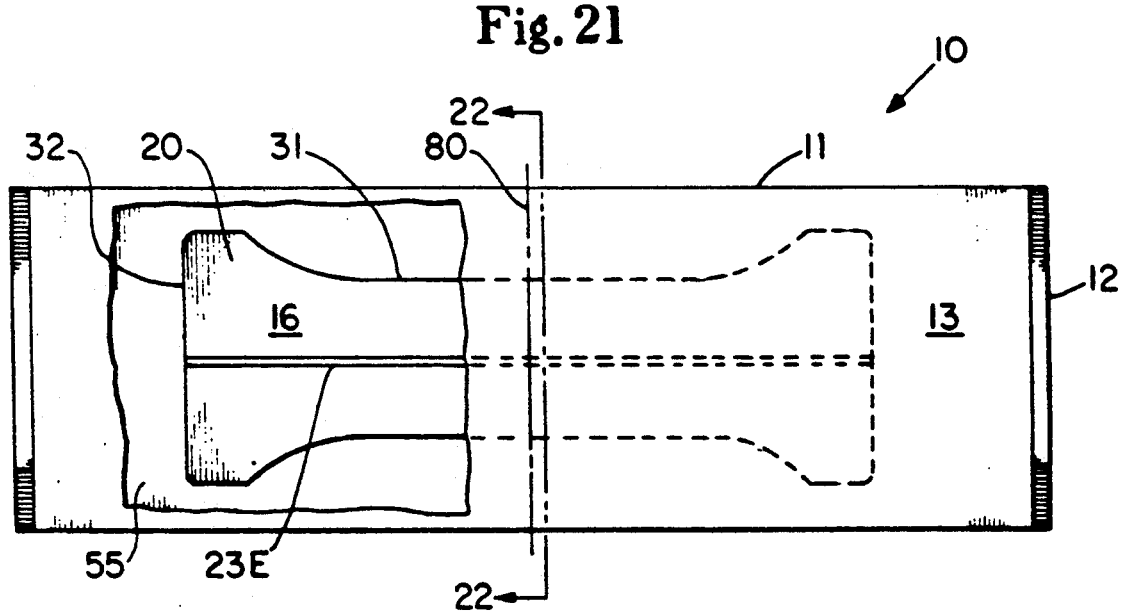
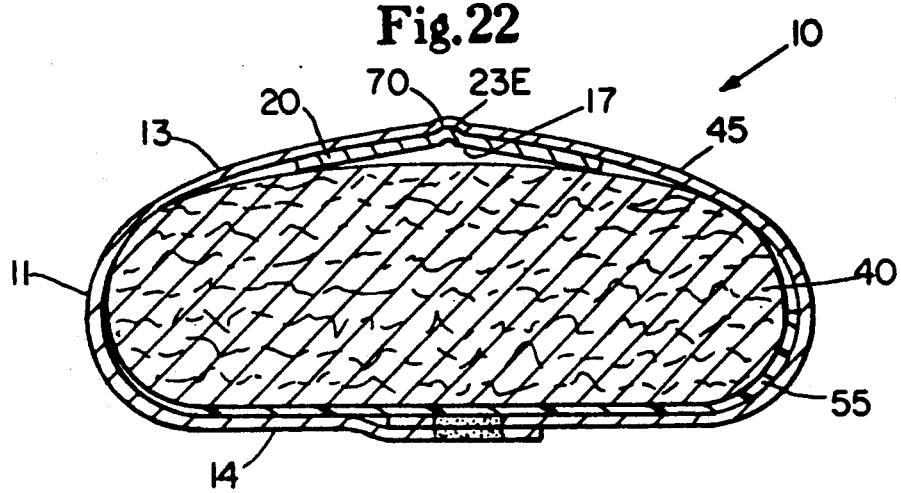

ABSORBENT ARTICLE HAVING A THERMOPLASTIC DEFORMABLE ELEMENT

This is a continuation of application Ser. No. 07/825,456, filed on Jan. 21, 1992 now U.S. Pat. No. 5,171,302 which is a continuation of application Ser. No. 07/175,817 filed on Mar. 31, 1988, abandoned.

BACKGROUND OF THE INVENTION

1. Field of the Invention

The present invention relates to disposable absorbent articles and more particularly to female sanitary napkins. Particularly, the present invention concerns sanitary napkins offering enhanced fit and comfort through a construction which promotes a continuously self-conforming anatomical cooperation of the sanitary napkin to the wearer to yield a highly effective absorbent device.

2. Background Art

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", which patent issued to Wiegner et al. on Nov. 1, 1983, and U.S. Pat. No. 4,413,986, entitled "Tampon Assembly With Means For Sterile Insertion", which patent issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", which patent issued to Arone on Sep. 7, 1937, and U.S. Pat. No. 3,905,372, entitled "Feminine Hygiene Protective Shield", which patent issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", which patent issued to Jacks on Dec. 15, 1953, and U.S. Pat. No. 4,631,062, entitled "Labial Sanitary Pad", which patent issued to Lassen et al. on Dec. 23, 1986.

With respect to sanitary napkins, at least three general classes of design exist. One such design includes those sanitary napkins which are generally cupped or boat-shaped and which are intended to catch menses as it runs or drips from the vaginal orifice. These sanitary napkins generally bow downwards, when worn, thus forming a cup-shape. Sanitary napkins of this class are disclosed in U.S. Pat. No. 3,570,493, entitled "Sanitary Towel", which patent issued to Olson on Mar. 16, 1971, and U.S. Pat. No. 4,655,759, entitled "Reduced Leakage Menstrual Pad With Built-in Fold Lines", which patent issued to Romans-Hess et al. on Apr. 7, 1987. A disposable urinary incontinence device which functions under the same principal is disclosed in U.S. Pat. No. 4,685,914, entitled "Disposable Urinary Pad", which patent issued to Holtman on Aug. 11, 1987.

A second class of sanitary napkin designs include those that are raised upwardly or humped in their medial portions so as to be near or in contact with the pudendal region when worn. These sanitary napkins attempt to contact and absorb menses immediately as it leaves the vestibule. Sanitary napkins of this class are disclosed in U.S. Pat. No. 2,064,431, entitled "Catamenial Bandage", which patent issued to Jurgensen on Dec. 15, 1936, U.S. Pat. No. 2,747,575, entitled "Catamenial Bandages", which patent issued to Mercer on May 29, 1956, U.S. Pat. No. 3,575,174, entitled "Sanitary Napkin", which patent issued to Mogor on Apr. 20, 1971, and U.S. Pat. No. 4,701,177, entitled "Three-Dimensional Shaped Feminine Pad With Narrow, Absorbent Center and Winged Edges", which patent issued to Ellis et al. on Oct. 20, 1987.

The third class of sanitary napkin designs include those that are not predisposed to have a trough or a hump shape when worn, but instead have a more or less rope-like shape when worn. Such sanitary napkins typically have a fluff pulp absorbent core surrounded by flexible outer wraps and when the sanitary napkin is subjected to compressive forces from the wearer's thighs the fluff pulp core simply compacts or bunches into an arbitrary, but generally rope-like shape. Sanitary napkins of this class are disclosed in U.S. Pat. No. 3,294,091, entitled "Sanitary Napkin", which patent issued to Morse on Dec. 27, 1966, U.S. Pat. No. 4,654,040, entitled "Smooth-Edged Contoured Sanitary Napkin", which patent issued to Luceri on Mar. 31, 1987, and U.S. Pat. No. 4,687,478, entitled "Shaped Sanitary Napkin With Flaps", which patent issued to Van Tilburg on Aug. 18, 1987. Attempts have been made to prevent the bunching effect of such compaction type sanitary napkins by providing them with a form-retaining member. Such sanitary napkins are disclosed in U.S. Pat. No. 4,195,634, entitled "Sanitary Napkin With Resilient Stiffening Means", which patent issued to DiSalvo et al. on Apr. 1, 1980, and U.S. Pat. No. 4,405,326, entitled "Catamenial Bandage", which patent issued to Lenaghan on Sep. 20, 1983.

While the sanitary napkins and other devices discussed above do provide some measure of success in absorbing and containing body exudates, they fail to address the need for a sanitary napkin which by the mere act of putting it on will itself merge in with, closely conform to and fit exactly the cross-sectional outline of the pudendal region as soon as applied without requiring the usual bending, twisting or other adjustments or manipulations, and which will always retain such conformity simply due to its flexure-resistant, reformable and resilient characteristics.

Therefore, it is an object of the present invention to provide a sanitary napkin which by the mere act of putting it on will itself merge in with, closely conform to, and fit exactly the cross-sectional outline of the external surfaces of the pudendal region.

It is an additional object of the present invention to provide a sanitary napkin which will change its shape so as to conform to the changing shape of the pudendal region when the wearer is running, squatting, crossing her legs, etc.

It is an additional object of the present invention to provide a sanitary napkin having a flexure-resistant deformation element which causes the body surface of the sanitary napkin to remain in intimate contact with the external surfaces of the labia majora.

It is an additional object of the present invention to provide a sanitary napkin having a flexure-resistant deformation element having a body facing surface wherein the body facing surface of the deformation element has a convex upward configuration when the napkin is subjected to the lateral compressive forces of the wearer's thighs.

It is an additional object of the present invention to provide a sanitary napkin having a flexure-resistant deformation element having a body facing surface wherein the body facing surface is generally cupped-shaped in the front region, generally "W" shaped in the central region and generally inverted "V" shaped in the back region of the deformation element.

These and other objectives of the present invention will be more readily apparent when considered in reference to the following description and when taken in conjunction with the accompanying drawings.

SUMMARY OF THE INVENTION

The present invention is directed to a disposable absorbent article, and particularly a sanitary napkin, having a flexure-resistant deformation element, the deformation element having a body facing surface which has a convex upward configuration when the sanitary napkin is worn. Primarily without relying on lateral compressive forces of the wearer's labia, the deformation element of the present invention relies on the lateral compressive forces of the wearer's thighs in order to form or maintain a convex upward configuration when the sanitary napkin is worn. In a preferred embodiment, the deformation element has a flexure means, and particularly a longitudinally extending flexure hinge, for inducing the body facing surface of the deformation element to have a convex upward configuration when the sanitary napkin is worn. In an alternatively preferred embodiment, the deformation element has a central region having a "W" shaped cross-section wherein the body facing surface of the deformation element having the convex upward configuration is located in the central region, generally symmetrically between the longitudinal side edges of the napkin. In another alternatively preferred embodiment, the deformation element has a cup-shaped front region and a back region having a convex upward configured body facing surface. The deformation element may be a moldable substance such as a foam, it may be reformable and/or it may be resilient.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements and in which:

FIG. 1 is a top plan view of a preferred sanitary napkin embodiment of the present invention with the portion of the sanitary napkin which contacts the wearer facing the viewer.

FIG. 2 is a side view of the preferred sanitary napkin embodiment shown in FIG. 1.

FIG. 3 is an end view of the preferred sanitary napkin embodiment shown in FIG. 1.

FIG. 4 is a lateral cross-sectional view of the preferred sanitary napkin embodiment shown in FIG. 1 taken along section line 4—4 of FIG. 1.

FIG. 20 is a depiction of the lateral cross-sectional view of the preferred deformation element embodiment shown in FIG. 16, depicting the deformation of the deformation element when the body surface of the preferred sanitary napkin embodiment of FIG. 1 makes intimate contact with the pudendal region of a wearer.

FIG. 21 is a top plan view of an alternatively preferred sanitary napkin embodiment of the present invention having portions cut away to reveal underlying structure and with the portion of the sanitary napkin which contacts the wearer facing the viewer.

FIG. 22 is a lateral cross-sectional view of the alternatively preferred sanitary napkin embodiment shown in FIG. 21 taken along section line 22—22 of FIG. 21.

DETAILED DESCRIPTION OF PREFERRED EMBODIMENTS

Figure 5:
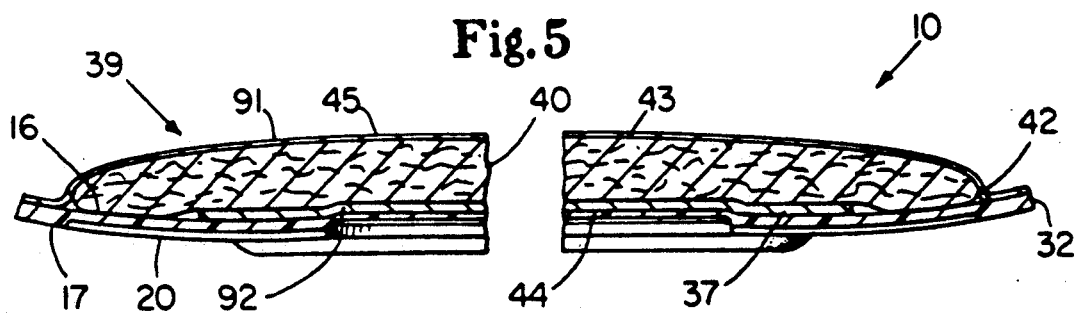
FIG. 5 is a longitudinal cross-sectional view of the preferred sanitary napkin embodiment shown in FIG. 1 taken along section line 5—5 of FIG. 1.

The present invention relates to disposable absorbent articles such as sanitary napkins, and in particular to sanitary napkins having a flexure-resistant deformation element having a convex upward configured body facing surface when worn.

As used herein, the term "disposable absorbent article" refers to articles which absorb and contain body exudates and more specifically refers to articles which are placed against or in proximity to the body of a wearer to absorb and contain the various exudates which are discharged from the body (e.g., blood, menses, urine) and which are intended to be discarded after a single use (i.e., they are not intended to be laundered or otherwise restored or reused). A preferred embodiment of the disposable absorbent article of the present invention is shown in FIGS. 1 through 5 as it would be used in a sanitary napkin 10. As used herein, the term "sanitary napkin" refers to an article which is worn by females adjacent to the pudendal region and which is intended to absorb and contain menstrual fluids and other vaginal discharges. Interlabial devices which reside partially within the wearer's vestibule are also within the scope of this invention. As used herein, the term "pudendal" refers to the externally visible female genitalia and is limited to the labia majora, the labia minora, the clitoris and the vestibule.

As can be seen in FIGS. 1 through 5, a preferred sanitary napkin 10 basically comprises a deformation element 20 and an absorbent means 39. The absorbent means 39 may be any means which is generally compressible, conformable, non-irritating to the wearer's skin and capable of absorbing and containing liquids and certain body exudates such as menses, blood and urine. If the absorbent means 39 is comprised of more than one constituent part or material, one part or material of the absorbent means 39 may not be absorbent or liquid permeable, so long as the combination of parts or materials has some degree of absorbency and some degree of the properties set forth above. The absorbent means 39 has a first major surface 91 and a second major surface 92. In the preferred embodiment illustrated, the deformation element 20 serves as the liquid impermeable backing for the sanitary napkin 10 and has a body facing surface 16, a bottom surface 17, and a periphery 33 which comprises the element side edges 31 and the element end edges 32. In the preferred embodiment shown in FIGS. 1 through 5, the absorbent means 39 is superimposed on the deformation element 20 such that the second major surface 92 of the absorbent means 39 is adjacent to the body facing surface 16 of the deformation element 20. Further, in the preferred embodiment shown in FIGS. 1 through 5, the absorbent means 39 comprises an absorbent core 40 and a liquid permeable topsheet 45. The absorbent core 40 has a first major surface 43, a second major surface 44, core side edges 41 and core end edges 42. The absorbent core 40 is superimposed on the deformation element 20 such that the second major surface 44 of the absorbent core 40 is adjacent to the body facing surface 16 of the deformation element 20. The topsheet 45 overlays the first major surface 43 of the absorbent core 40.

The sanitary napkin 10 has a liquid receiving body surface 13 which is generally defined by the topsheet 45 and a garment surface 14 which is generally defined by the bottom surface 17 of the deformation element 20. Preferably the topsheet 45 and the deformation element 20 have length and width dimensions generally larger than the absorbent core 40 so that they extend beyond the core side edges 41 and the core end edges 42 of the absorbent core 40 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. The extension of the topsheet 45 and/or the deformation element 20 beyond the core side edges 41 and the core end edges 42 of the absorbent core 40 forms the longitudinal side edges 11 and the end edges 12, respectively, of the sanitary napkin 10. The longitudinal side edges 11 and the end edges 12 of the sanitary napkin 10 comprise the periphery 15 of the sanitary napkin 10.

Looking at some of the members of the sanitary napkin 10 more specifically, the topsheet 45 is positioned adjacent the first major surface 43 of the absorbent core 40 and overlays a major portion of the absorbent core 40 so that when exudates are discharged onto the topsheet 45 they will transfer from the body surface 13 of the topsheet 45 through to the absorbent core 40 where they are absorbed by the absorbent core 40. The topsheet 45 extends outwardly toward the edges of the absorbent core 40 so that a major portion of the absorbent core 40 is disposed between the topsheet 45 and the deformation element 20. In the preferred embodiment shown in FIGS. 1 through 5, the topsheet 45 has length and width dimensions generally larger than those of the absorbent core 40.

The topsheet 45 is compliant, soft feeling, and non-irritating to the wearer's skin. Further, the topsheet 45 is liquid pervious, permitting liquids to readily transfer through its thickness. A suitable topsheet 45 may be manufactured from a wide range of materials such as formed thermoplastic films, apertured plastic films, porous foams, reticulated foams, natural fibers (e.g., wood or cotton fibers), synthetic fibers (e.g., polyester or polypropylene fibers) or from a combination of natural and synthetic fibers, with formed films being preferred. Formed films are preferred for the topsheet 45 because they are pervious to liquids and yet non-absorbent. Thus, the surface of the formed film, which is in contact with the body, remains dry, thereby reducing body soiling and creating a more comfortable feel for the wearer. Suitable formed films are described in U.S. Pat. No. 3,929,135, entitled "Absorptive Structure Having Tapered Capillaries", which patent issued to Thompson on Dec. 30, 1975, U.S. Pat. No. 4,324,246, entitled "Disposable Absorbent Article Having A Stain Resistant Topsheet", which patent issued to Mullane and Smith on Apr. 13, 1982, U.S. Pat. No. 4,342,314, entitled "Resilient Plastic Web Exhibiting Fiber-Like Properties", which patent issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which patent issued to Ahr, Louis, Mullane, and Ouellete on Jul. 31, 1984, all of which patents are incorporated herein by reference.

In a preferred embodiment of the present invention, the body surface 13 of the topsheet 45 is hydrophilic. The hydrophilic body surface 13 helps liquid to transfer through the topsheet 45 faster than if the body surface 13 was not hydrophilic. This diminishes the likelihood that menstrual fluid will flow off the topsheet 45 rather than being absorbed by the absorbent core 40. In a preferred embodiment, the body surface 13 of the topsheet 45 is made hydrophilic by treating the body surface 13 with a surfactant. It is preferred that the surfactant be substantially evenly and completely distributed throughout the body surface 13 of the topsheet 45. This can be accomplished by any of the common techniques well known to those skilled in the art. For example, the surfactant can be applied to the topsheet 45 by spraying, by padding or by the use of transfer rolls.

In addition, in a preferred embodiment, as illustrated in FIG. 1, the topsheet 45 may advantageously be provided with a target acquisition zone 46. As shown in FIG. 1, the zone 46 has larger openings and a greater percentage of open area than the remaining regions of the topsheet 45. The zone 46 serves two purposes. First, the larger openings and greater open area provide quicker acquisition of fluid gushes which are often experienced when a women rises from having been seated or lying, whereas blood and menses have accumulated in the vaginal canal or vestibule. Second, the larger openings of the zone 46, as compared to the rest of the topsheet 45, provide more complete acquisition of the sometimes highly viscous menses. Without the zone 46, less absorption of exudates may take place and the unabsorbed exudates may lay in contact with the body and cause irritation or they may flow to the edges 11 and 12 of the sanitary napkin 10 and cause soiling. The zone 46 can be positioned anywhere on the topsheet 45 and can have any shape. The zone 46 can be as small as proper functioning will allow or almost as large as the topsheet 45, itself. However, because the larger openings of the zone 46 may not prevent rewet as well as the rest of the topsheet 45, the zone 46 preferably has an area great enough to be in contact with the menses as it exits the vestibule yet not so large as to contact surrounding skin surfaces which could be soiled or irritated by rewet.

Preferably, as shown in FIG. 1, the zone 46 is positioned on the topsheet 45 in an area where menses will contact the zone 46 first before contacting the rest of the topsheet 45. This area is preferably disposed beneath the vestibule and more preferably beneath the vaginal orifice. In the preferred embodiment of the topsheet 45 shown in FIG. 1, the target acquisition zone 46 is symmetrically located on the topsheet 45 due to the fact that the preferred embodiment of the napkin 10 shown is designed symmetrically so that the napkin 10 and the target acquisition zone 46 will function properly, when worn, no matter which direction the napkin 10 is worn.

As seen in FIG. 1, the perimeter of the target acquisition zone 46 is defined by an inner perimeter region 47. In the preferred embodiment shown, the inner perimeter region 47 is impervious. The inner perimeter region 47 may be formed by thermomolding a polymeric topsheet 45 to a polymeric fiber absorbent core 40 or by gluing or fusing a topsheet 45 to a fluff pulp absorbent core 40. The inner perimeter region 47 is not primarily intended for the function of defining the outer perimeter of the zone 46, but, instead is intended to hold the topsheet 45 in contact with the absorbent core 40 so that the topsheet 45 will not shift or roll, and also so that the absorbent core 40 will stay in place and have better integrity. Further, the inner perimeter region 47 may not be liquid impervious but will function equally well if it is liquid pervious. In the preferred embodiment shown in FIG. 1, the configuration of the inner perimeter region 47 is made to correspond to the outline of the protuberance 71 of the deformation element 20, which will be explained in more detail later in this specification. The inner perimeter region 47 creates a slight trough around the zone 46 causing the zone 46 to have a somewhat pillowing effect. In an alternative embodiment of the napkin 10, the deformation element 20 has dimples in regions which correspond to the inner perimeter region 47 and which extend through the absorbent core 40, in which case the topsheet 45 is thermomolded or glued directly to the dimples.

The absorbent core 40 may be any means which is generally compressible, conformable, non-irritating to the wearer's skin, and capable of absorbing and containing liquids and certain body exudates. The absorbent core 40 may be manufactured in a wide variety of sizes and shapes (e.g., rectangular, hourglass, etc.) and from a wide variety of liquid absorbent materials commonly used in disposable sanitary napkins, diapers and other absorbent articles, such as comminuted wood pulp which is generally referred to as airfelt and which is preferred. Examples of other suitable absorbent materials include creped cellulose wadding, absorbent foams, absorbent sponges, super absorbent polymers, absorbent hydrogel materials, polymeric fibers, or any equivalent materials or combinations of materials. The total absorbent capacity of the absorbent core 40 should, however, be compatible with the design exudate loading for the intended use of the absorbent article. Further, the size and absorbent capacity of the absorbent core 40 may be varied to accommodate wearer's ranging in size and also ranging in the expected amount of exudate fluid volume. For instance, a different absorbent capacity may be utilized for sanitary napkins intended for daytime use as compared with those intended for nighttime use or for sanitary napkins intended for use by teenage females as compared with those intended for use by more mature women.

A preferred embodiment of the sanitary napkin 10 has a generally rectangular shaped absorbent core 40 having rounded end edges 42 and is intended to be worn by generally all females. The absorbent core 40 is preferably a batt of airfelt having a laminate of hydrogel forming material 37 adjacent to and underlaying the airfelt fibers. Suitable hydrogel forming materials are disclosed in U.S. Pat. No. 4,654,039, entitled "Hydrogel-Forming Polymer Compositions For Use In Absorbent Structures", which patent issued to Brandt, Goldman and Inglin on Mar. 31, 1987. Preferably, the batt of airfelt is about 6.0 centimeters wide (lateral dimension) and about 19.0 centimeters long (longitudinal dimension). The absorbent core 40 has a generally uniform caliper of about 4.6 millimeters, an absorbent capacity of from about 4.0 grams to about 10.0 grams of water per gram of absorbent material and a density of about 0.1 grams per cubic centimeter. It should be understood, however, that the size, shape, configuration, and total absorbent capacity of the absorbent core 40 may be varied to accommodate wearer's ranging in size and expected fluid flow. Therefore, the dimensions, shape, and configuration of the absorbent core 40 may be varied (e.g., the absorbent core may have a varying caliper or a hydrophilic gradient).

The deformation element 20 is flexure-resistant. As used herein, the term "flexure-resistant" refers to an element which will support a bending moment, in contrast to an element which will support only axial forces. The deformation element 20 of the present invention has a preference for having a convex upward configuration when the napkin 10 is subjected to lateral compressive forces 100, when worn. Preferably, the deformation element 20 of the present invention will have a convex upward configuration when the sanitary napkin 10 is worn by different females wearing the same designed napkin 10 for a period of fifteen minutes in at least seventy of one-hundred trials. In some configurations of the element 20, the wearer may have to initially manipulate the element 20 into a convex upward configuration either prior to or just after placement of the napkin 10 to the wearer's body. Preferably, the deformation element 20 is manufactured from a moldable substance. More preferably the element 20 is manufactured from a thermomoldable substance, and most preferably a radiation cross-linked polyethylene foam. Such a foam is manufactured by Voltek, Inc. of Lawrence, Massachusetts, and marketed in the trade as Voltek Volara Type 2A. Another suitable foam is a thermomoldable cross-linked closed cell polyolefin which is manufactured by Dynamit Nobel of America, Inc. of South Holland, Ill., and marketed in the trade as Dynamit Nobel Trocellen Type XJV400. A preferred deformation element 20 has a caliper of from about 1.25 to about 2.5 millimeters and more preferably from about 1.75 to about 2.0 millimeters. A preferred element 20 is formed from a polyethylene foam sheet which is subsequently subjected to molding by a known thermomolding process. The sheet is subjected to thermomolding at a temperature of from about 110° C. to about 205° C. to form the element 20. Other suitable foams are made from such substances as polyethylene, polypropylene, polyester, polybutylene, ethylene vinyl acetate, polyurethane, thermobondable cellulose, latex, silicone elastomerics and others. However, the element 20 need not be made of foam. Alternatively, the element 20 could be made of fibers, films or sheets of cellulose, rayon, nylon, polyester, stiffened cotton, polyethylene, vinyl acetate, latex, rubber, plastic, heavy-weight paper such as cardboard, coated paper, or a combination or laminate of these or other materials. Further, if the element 20 is susceptible to being wetted when worn, then the element 20 must be moisture stable. In other words, elements which are susceptible to wetting when worn and are not moisture stable, but instead are moisture unstable, are not within the scope of the present invention. As used herein, the term "moisture unstable" refers to materials which are held together solely by hydrogen bonds and/or fibrous structures comprised of short fibers having a length of 10.0 millimeters or less which are held together by mechanical entanglement and frictional forces. An example of a material which is held together solely be hydrogen bonds is standard toilet tissue which is a slurry of wood pulp laid on a screen and subjected to drying. An example of a material which is held together by mechanical entanglement and frictional forces is short-fiber fluff pulp which is air-laid and then compressed or densified to promote interfiber entanglement. Conversely, if a material is bonded at least partially through means other than hydrogen or short-fiber mechanical entanglement and frictional forces, then the material is moisture stable. Examples include short wood pulp fibers which are adhesively held together, foams having chemical bonds other than just hydrogen, long synthetic fibers suitably blended with short-fiber wood pulp and others. The reason that the element 20 must be moisture stable is that in order for the element 20 to provide continuing benefit when worn and soiled, the element 20 should maintain a functional degree of flexure-resistance throughout a normal wearing time. While it is true that many moisture unstable elements form up nicely into a convex upward configuration and have flexural-resistance prior to or shortly after being worn, when these elements are subjected to perspiration, water, menses or urine in the presence of wearing flexures, their hydrogen or mechanical frictional bonds deteriorate and the element loses a large part, if not all, of its flexure-resistance and, therefore, its usefulness.

Of course, a number of ingenious embodiments of the present invention exist in which the deformation element 20 does not consist solely of a single homogenous material. For example, the element 20 may be comprised of fluff pulp having unbonded regions and selected adhesively bonded regions which impart to the element 20 a flexure-resistance. Alternatively, the element 20 may be comprised of fluff pulp having thin strips or a lattice of foam material dispersed throughout the fluff pulp to provide flexure-resistance. Also, for example, the element 20 may be a polymeric sheet having a stiffening grid bonded to it to provide flexure-resistance. In such cases where the element 20 is a combination of materials, if it is necessary to test the flexure-resistance of the element 20 by the Circular Bend Procedure, as explained below, then each constituent part should be tested individually, if feasible, and also the combination of materials should be tested as a whole.

Preferably, the element 20 has a flexure-resistance measured by peak bending stiffness of at least about 100.0 grams. More preferably, the deformation element 20 has a peak bending stiffness of greater than about 200.0 grams, and most preferably greater than about 350.0 grams. Depending on the element's 20 design, peak bending stiffnesses of greater than 500.0 grams have been found acceptable. As an element increases in flexure-resistance, it generally maintains its shape better, but it also generally becomes more uncomfortable and increases wearing awareness.

Peak bending stiffness is determined by a test which is modeled after the ASTM D 4032-82 CIRCULAR BEND PROCEDURE, the procedure being considerably modified and performed as follows. The circular bend procedure is a simultaneous multi-directional deformation of a material in which one face of a specimen becomes concave and the other face becomes convex. The circular bend procedure gives a force value related to flexure-resistance, simultaneously averaging stiffness in all directions.

APPARATUS:

The apparatus necessary for the CIRCULAR BEND PROCEDURE is a modified Circular Bend Stiffness Tester, having the following parts:

Two smooth-polished steel plate platforms which are 102.0×102.0×6.35 millimeters, one having an 18.75 millimeter diameter orifice and the other having a 31.75 millimeter diameter orifice. The lap edge of each orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force-measurement gauge, and more specifically an Instron inverted compression load cell. The load cell has a load range from about 0.0 to about 2000.0 grams.

An actuator, and more specifically the Instron Model No. 1122 having an inverted compression load cell. The Instron 1122 is made by the Instron Engineering Corporation, Canton, Mass.

NUMBER AND PREPARATION OF SPECIMENS

In order to perform the procedure for this test, as explained below, five representative absorbent articles are necessary. From each absorbent article, the element to be tested is removed. In articles where the deformation element 20 is a combination of materials, as earlier explained, each constituent part should be tested separately, if feasible, and also, the element should be tested as a whole. From one of the five elements to be tested, some number "Y" of 37.5×37.5 millimeter test specimens are cut. If any portion of the element meets the parameters of this test, then the element as a whole satisfies the test. Therefore, a number "Y" of different specimens should be tested from each element. Certainly, the structurally most rigid portion of the element should be tested. Preferably, a test specimen is cut from a portion of the element which has a convex upward configuration, as later described. There may be portions of the elements which are not 37.5×37.5 millimeters. In such a case, the largest available specimen of the element should be tested. The test specimens should not be folded or bent by the test person and the handling of specimens must be kept to a minimum and to the edges to avoid affecting flexural-resistance properties. From the four remaining elements, an equal number "Y" of 37.5×37.5 millimeter specimens identical to the specimens cut from the first element are cut. Thus, the test person should have "Y" number of sets of five identical specimens.

PROCEDURE

The procedure for the CIRCULAR BEND PROCEDURE is as follows. The specimens are conditioned by leaving them in a room which is 21±1° C. and 50±2% relative humidity for a period of two hours. It has been recognized that specimens having an uncompressed optical caliper of 6.35 millimeters or greater tend to bunch up in the 18.75 millimeter test plate orifice and thereby give readings which are more related to the specimen's compression resistance rather than the specimen's flexure-resistance. Thus, specimens having an uncompressed optical caliper of 6.35 millimeters or greater should be tested using the test plate having the orifice of 31.75 millimeters. Whichever plate is used, the test procedure and calculations remain the same and the preferred flexure-resistances previously given also remain the same. The tester plate is leveled. The plunger speed is set at 50.0 centimeters per minute per full stroke length. A specimen is centered on the orifice platform below the plunger such that the body facing surface 16 of the specimen is facing the plunger and the bottom surface 17 of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the specimens have been tested.

CALCULATION

The peak bending stiffness for each specimen is the maximum force reading for that specimen. Remember that "Y" number of sets of five identical specimens were cut. Each set of five identical specimens are tested and the five values received are averaged. Thus, the test person now has an average value for each of the "Y" sets tested. Remember, if any portion of the element satisfies this test, then the element as a whole satisfies the test. Therefore, the flexure-resistance for a particularly designed element is the greatest of these average peak bending stiffnesses.

In the preferred embodiment of the sanitary napkin 10 shown in FIGS. 1 through 5, the deformation element 20 is positioned such that the body facing surface 16 of the deformation element 20 is adjacent to the second major surface 44 of the absorbent core 40. In the preferred embodiment, the deformation element 20 is substantially liquid impermeable and serves as the liquid impermeable backing of the sanitary napkin 10. The deformation element 20 underlays a major portion of the absorbent core 40 so that exudates which are absorbed by and contained within the absorbent core 40 are prevented from soiling adjacent garments and linens. In the preferred embodiment, the deformation element 20 has length and width dimensions generally larger than the absorbent core 40 so that the deformation element 20 extends beyond the core side edges 41 and the core end edges 42 to the longitudinal side edges 11 and the end edges 12, respectively, of the sanitary napkin 10 where it is associated with the topsheet 45. In a preferred embodiment, the topsheet 45 and the deformation element 20 are heat-sealed to each other near and along the periphery 15 of the sanitary napkin 10.

In a preferred embodiment, the foam element 20 has a closed-cell construction on its body facing surface 16 so that it is non-absorbent. However, the foam element 20 may be of an open-cell construction on its body facing surface 16 so that it is absorbent. However, when the foam element 20 is used as the liquid impermeable backing of the sanitary napkin 10, the element 20 should be substantially liquid impermeable.

Figure 6:
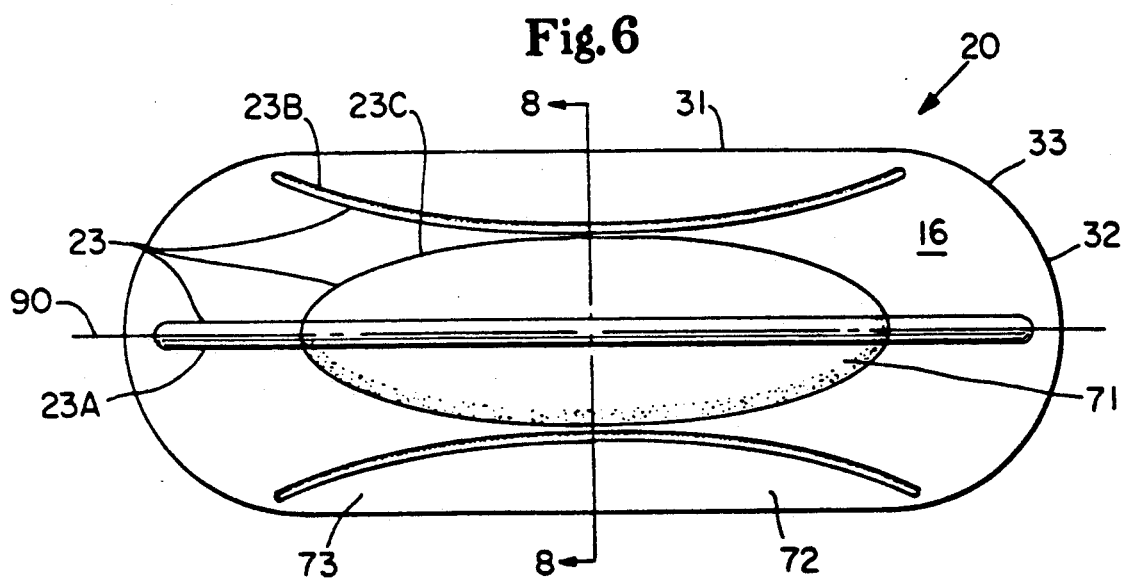
FIG. 6 is a top plan view of a preferred deformation element embodiment of the preferred sanitary napkin embodiment shown in FIG. 1.
Figure 7:
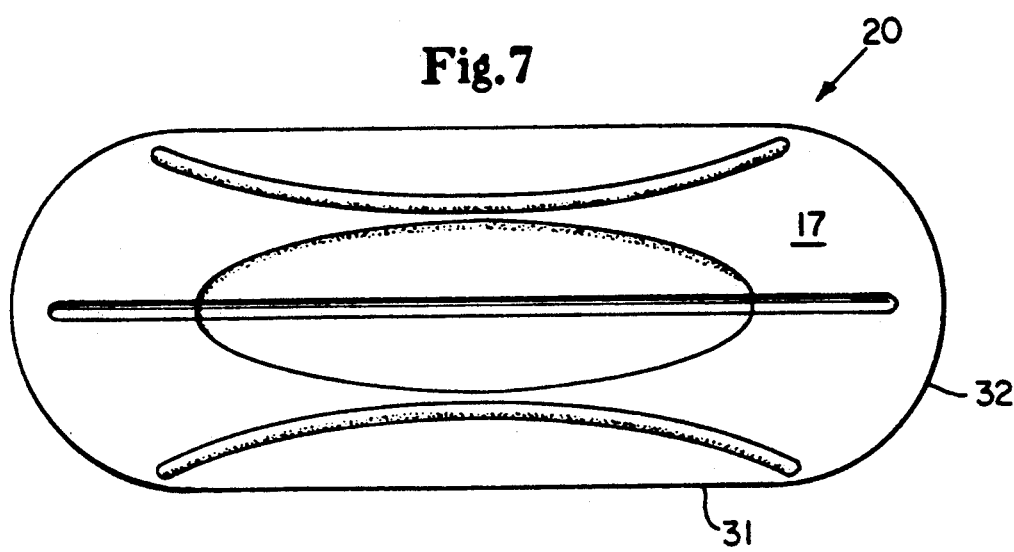
FIG. 7 is a bottom plan view of the preferred deformation element embodiment shown in FIG. 6.
Figure 8:
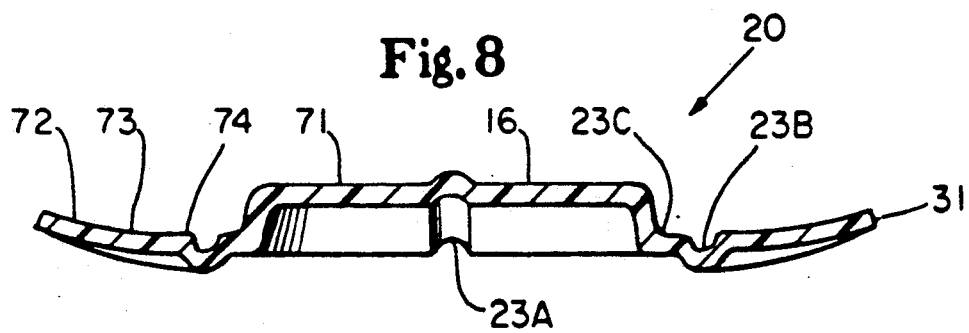
FIG. 8 is a lateral cross-sectional view of the preferred deformation element embodiment shown in FIG. 6 taken along section line 8—8 of FIG. 6.

A preferred deformation element 20 of the sanitary napkin 10 shown in FIGS. 1 through 5 is shown in FIGS. 6 through 8. In the preferred embodiment, the element 20 has a length of about 20.5 centimeters, a width of about 8.0 centimeters and a generally uniform caliper of about 2.0 millimeters, except for the flexure hinges 23A, 23B and 23C which have a caliper of about 1.25 millimeters. In a preferred embodiment, the deformation element 20 has a flexure means 23 for inducing the deformation element 20 to bend in a preconceived way into a preconceived geometric configuration when the sanitary napkin 10 is subjected to lateral compressive forces 100 when worn. There are a number of possible flexure means 23. A preferred flexure means 23 are the flexure hinges 23A, 23B and 23C shown in FIGS. 6 through 8. A flexure hinge initiates deformational development of preconceived geometric configurations. A flexure hinge creates different bend-resistances across the width of the deformation element 20. The difference in bend-resistance can be created by geometric discontinuities in the element 20 as by pre-set folds, scoring, indentations, perforations, or fairly abrupt changes in elevation. The difference can also be created by changes in bend-resistance across the width of the element 20 due to changes in material properties of the element 20 as by localized compaction or by the combination of different materials across the width of the element 20, wherein the materials have different flexure-resistances. In a preferred embodiment, the flexure hinges 23A, 23B and 23C induce the deformation element to have a convex upward configuration when the napkin 10 is worn. The convex upward configuration of the element 20 causes the absorbent core 40 and the topsheet 45 to also have a convex upward configuration, and consequently, the body surface 13 of the napkin 10 has a convex upward configuration when the napkin 10 is worn.

The preferred embodiment of the element 20 shown in FIGS. 6 through 8 has a linear central hinge 23A, a pair of curvilinear thigh hinges 23B, and a pair of curvilinear protuberance hinges 23C, all of which are of the geometric discontinuous type and all of which have been thermomolded into the element 20. From each element side edge 31, the element 20 slopes inwards and downwards to form walls 72 having bases 74 which are adjacent to the curvilinear thigh hinges 23B. The walls 72 comprise that portion of the element 20 between the thigh hinges 23B and the element side edges 31. The walls 72 have a pudental facing surface 73. FIGS. 6 and 7 illustrate that the thigh hinges 23B extend generally longitudinally and curve inward from the element side edges 31 so as to approximate the curvature of a wearer's thighs. In other words, the thigh hinges 23B are arcuate, wherein the midpoint of the arc is the greatest distance from the element side edges 31. The thigh hinges 23B have a generally "U" shaped cross-section as shown in FIG. 8. Adjacent to the longitudinal midpoint of the thigh hinges 23B are the curvilinear protuberance hinges 23C which serve to define the perimeter of the protuberance 71 of the element 20 as shown in FIGS. 6 and 7. The protuberance hinges 23C are arcuate wherein the midpoint of the arc is the greatest distance from the longitudinal axis 90. The protuberance hinges 23C are formed into the element 20 as a result of the thermomolding formation of the protuberance 71. Thus, as shown in FIG. 8, the protuberance hinges 23C are the result of a fairly abrupt change in elevation across the element 20. As shown in FIG. 8, from the protuberance hinges 23C the element 20 curvilinearly slopes upward to the linear central hinge 23A, thus forming a protuberance 71. The protuberance 71 is provided to promote and initiate some of the desired bending deformations of the element 20 and, in particular, the protuberance 71 predisposes the element 20 to bend in such a way that the body facing surface 16 of the element 20 will have a convex upward configuration when the napkin 10 is subjected to lateral compressive forces 100 when worn, as will be later explained. Of course, the protuberance 71 need not be provided and, in fact, the element 20 can be planar or downwardly cup shaped. However, such configurations might require a more complex design that might require more compressive force and more mechanical action in order to create a convex upward configuration. Thus, by providing the element 20 with a protuberance 71 and thereby giving the body facing surface 16 of the element 20, and more particularly that portion of the body facing surface 16 which is superimposed over the protuberance 71, a pre-formed convex upward configuration, the element 20 need only maintain a convex upward configuration when the napkin 10 is subjected to lateral compressive forces 100, when worn, in contrast to an element 20 that is planar or downwardly cupped shaped when applied but assumes a convex upward configuration when worn. As used herein, the term "maintain" includes embodiments wherein the body facing surface 16 of the element 20 retains the same convex upward configuration that it had prior to the application of lateral compressive forces 100 when worn and embodiments wherein the body facing surface 16 assumes a different convex upward configuration than it had prior to the application of lateral compressive forces 100 when worn. In addition, recognizing that an object of the present invention is to put the body surface 13 of the napkin 10 in intimate contact with the external surfaces of the labia majora when worn, the protuberance 71 gives the element 20 and, consequently the napkin 10, some pre-formed elevation to aid in providing such intimate contact. As seen in FIGS. 6 and 7, the central hinge 23A extends longitudinally along the longitudinal axis 90 of the element 20 nearly from one end edge 32 of the element 20 to the other end edge 32. As shown in FIG. 8, the central hinge 23A has a generally inverted "U" shaped cross-section.

The previous description of the sanitary napkin 10, and particularly the deformation element 20, has been directed to the element's 20 "at rest" configuration. However, when the sanitary napkin 10 is worn, at least a portion of the body facing surface 16 of the deformation element 20 must have a convex upward configuration. As used herein, the term "convex upward configuration" includes embodiments wherein at least a portion of the body facing surface 16 of the deformation element 20 has a convex shape.

Figure 10:
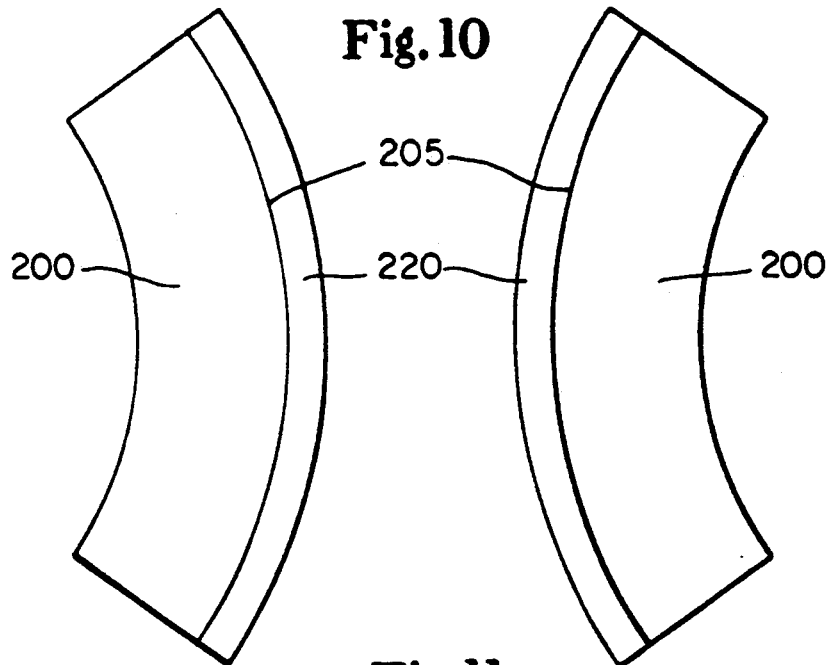
FIG. 10 is a top plan view of the test apparatus plungers.
Figure 11:
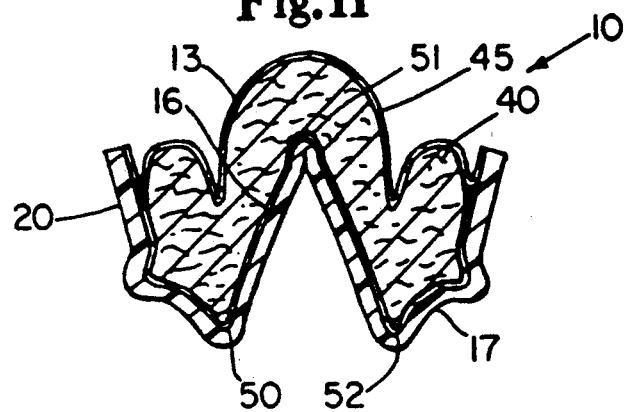
FIG. 11 is a view of a cast molded lateral cross-section of the preferred sanitary napkin embodiment shown in FIG. 1 when the sanitary napkin is being worn, the cross-section being taken along the lateral centerline of the sanitary napkin.
Figure 14:
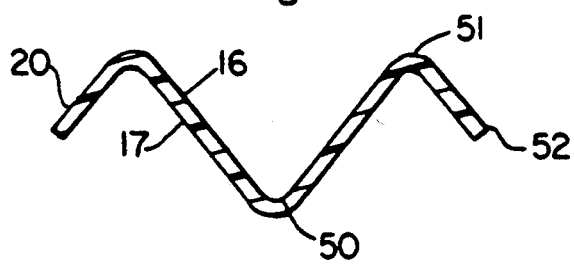
FIG. 14 is a lateral cross-sectional view of an alternatively preferred deformation element embodiment of an alternatively preferred sanitary napkin embodiment of the present invention which is being worn, the cross-section being taken through that portion of the sanitary napkin which is disposed beneath the center of the vaginal orifice when the sanitary napkin is worn.
Figure 15:
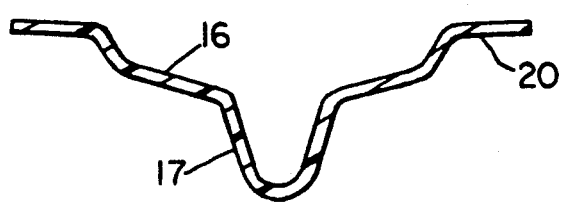
FIG. 15 is a lateral cross-sectional view of a deformation element of a sanitary napkin which is being worn, the sanitary napkin not being within the scope of the present invention.

The presence of a "convex upward configuration" is determined as follows, the following explanation being given with reference to FIGS. 9 through 11. First, two plungers 200 having a radius of about 76.2 millimeters are positioned symmetrically across from each other so that the midpoint of the faces of the plungers 200 are about 25.4 millimeters apart. The curvature of the plungers 200 is intended to approximate the curvature of the thighs of a representative number of women. The 25.4 millimeters distance is intended to approximate the distance between the thighs of a representative number of women, when standing. A top view of two properly positioned plungers 200 is shown in FIG. 10. The plungers 200 have a face 205 height of about 51.0 millimeters, a bottom lip 220 having a width of about 5.0 millimeters and a thickness of about 5.0 millimeters. With the body surface 13 of the napkin to be tested facing up and the napgarment surface 14 of the napkin facing down, the napkin is placed between the plungers 200 in the shape that the napkin 10 generally has when worn. The napkin may have to be manipulated into its "in use" shape. Often, this "in use" shape can be determined through simple visual observations of females wearing the napkin. If the shape is not determinable through visual observation, at least one feasible alternative that is available is Magnetic Resonance Imaging (MRI). Magnetic resonance images of females wearing sanitary napkins which have been saturated with mineral oil have been used to give accurate depictions of the shape a sanitary napkin has when worn. As soon as the sanitary napkin is properly positioned between the plungers 200, a cast molding of the sanitary napkin is made. The cast molding is for the purpose of permanently "freezing" the napkin in this "in use" configuration so that the napkin can be further studied. The cast mold can be made from a number of different materials. Preferably, the material that is used will penetrate into the absorbent means. Two materials that have been found suitable are a hard-casting material which is marketed as EnviroTex 1 to 1 Polymer Coating by Environmental Technology, Inc. of Fields Landing, Calif. and a soft-casting material which is a mixture of 46% Veisamid 125 resin which is marketed by the Henkel Corporation of Minneapolis, Minn., 31% EPON 812 hardener which is marketed by Polaron Equipment Limited of Watford, Conn. and 23% 1,1,1 Trichloroethane thinner. The casting material can be poured directly into the napkin if the "in use" configuration is susceptible to such (i.e., for example, boat or cupped shaped). If not, a thin sheet of aluminum foil can be placed around and under the napkin so as to create a receiver for the casting material. The aluminum foil receiver can then be filled so as to submerge the napkin in the casting material. Either way, the napkin should substantially retain its in-use shape. After the casting material has set, any number of lateral cross-sections can be cut along the longitudinal length of the napkin. From these lateral cross-sections, a person can determine whether the napkin has a convex upward configuration by performing the following test, reference being directed to the cast molded lateral cross-section of the napkin 10 shown in FIG. 11. While looking directly at a cross-section, if there is a point on the body facing surface 16 of the element 20 that has an elevation of at least about 2.5 millimeters above either outer perimeter of the body facing surface 16, then the body facing surface 16 of the element 20 has a convex upward configuration. If there is such a point, the point is preferably at least about 5.0 millimeters above either outer perimeter of the body facing surface 16. If there is no such point, as per the lateral cross-section shown in FIG. 11, then, starting from the left outer perimeter of the body facing surface 16 of the element 20 and moving to the right, the body facing surface 16 is scanned until an inflection point 50 between a downward slope and an upward slope is found. If there is a first point 51 along the body facing surface 16 to the right of the infection point 50 which has an elevation of at least about 2.5 millimeters above the inflection point 50, and a second point 52 along the body facing surface 16 to the right of the first point 51 which has an elevation below the first point 51 of at least about 2.5 millimeters, as per the lateral cross-section shown in FIG. 11, then the body facing surface 16 of the deformation element 20 has a convex upward configuration. Preferably, the first point 51 has an elevation of at least about 5.0 millimeters above the inflection point 50 and the second point 52 has an elevation of at least about 5.0 millimeters below the first point 51. The body facing surface 16 must have at least one convex upward configuration but can have more. Preferably, a portion of the body facing surface 16 of the element 20 in the central region 62 of the element 20 will have a convex upward configuration. More preferably, the portion of the body facing surface 16 of the element 20 which is disposed beneath the center of the vaginal orifice when the napkin 10 is worn will have a convex upward configuration. A cross-section of an alternatively preferred deformation element 20 embodiment of the present invention having a body facing surface 16 having a convex upward configuration is shown in FIG. 14. An example of a deformation element 20 not within the scope of the present invention having a body facing surface 16 but not having a convex upward configuration is shown in FIG. 15.

Heretofore, the sanitary napkin 10, and particularly the deformation element 20, have basically been described in their "at rest" (i.e., not worn) configurations. However, because the general population of women have thighs which are too close together not to apply any laterally compressive forces 100 to the napkin 10 when worn, the "at rest" configurations of the napkin 10 and the element 20 will seldom, if ever, be realized when the napkin 10 of the present invention is being worn. Therefore, the following is a description of the different anatomy conforming shapes the deformation element 20 assumes along the element's 20 length when the sanitary napkin 10 is being worn and thereby subjected to the lateral compressive forces 100 of the wearer's thighs. In the preferred embodiment of the sanitary napkin 10 illustrated in FIGS. 1 through 13 and 16 through 20, the absorbent means 39 which is associated with the element 20, the generally flexes in cooperation with the element 20. More specifically, the topsheet 45, which is affixed directly to the element 20 in the periphery 15 of the napkin 10, and the absorbent core 40, which is disposed between the topsheet 45 and the element 20, generally flex in cooperation with the element 20. Thus, in the preferred embodiment, the cross-sectional configurations of the napkin 10 along the napkin's 10 longitudinal length, and specifically of the absorbent means 39, which in the preferred embodiment comprises the topsheet 45 and the absorbent core 40, generally mimic the cross-sectional configurations of the element 20. In other embodiments, the cross-sectional configurations of the napkin 10 and the absorbent means 39 may not mimic the cross-sectional configurations of the element 20.

Figure 12:
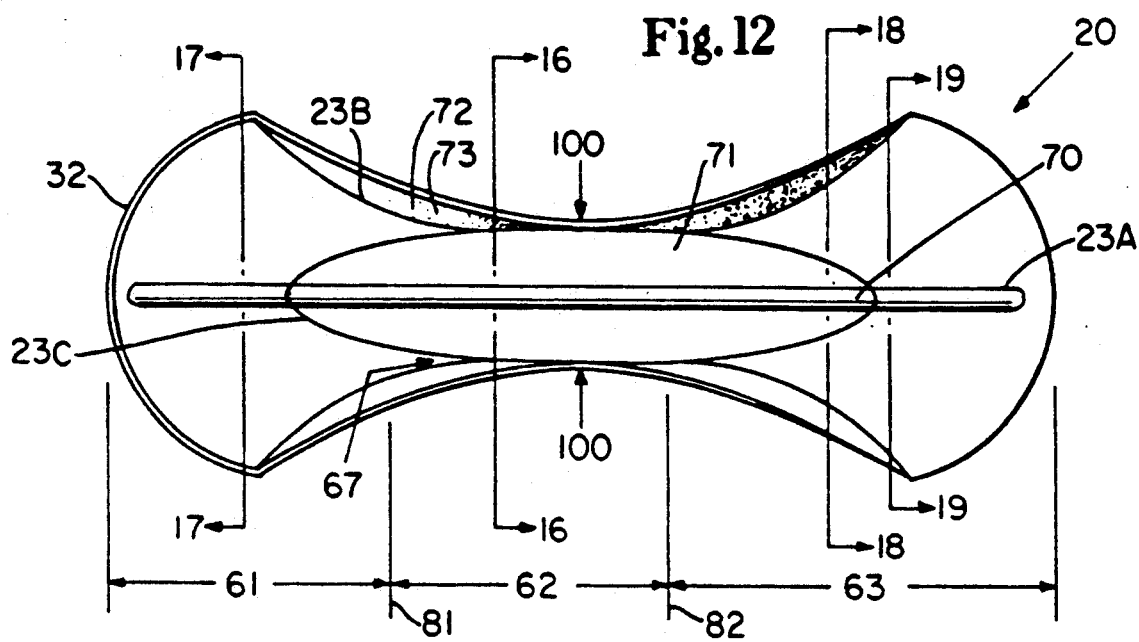
FIG. 12 is a top plan view of the preferred deformation element embodiment shown in FIG. 6 when the preferred sanitary napkin embodiment shown in FIG. 1 is being worn by a female who is naked and in the standing position with the sanitary napkin being subjected to lateral compressive forces by the wearer's thighs.
Figure 13:
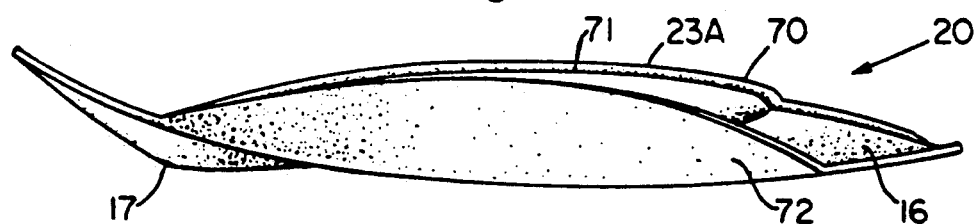
FIG. 13 is a side view of the preferred deformation element embodiment shown in FIG. 12.

As seen in FIG. 12, when a preferred embodiment of the sanitary napkin 10 is subjected to lateral compressive forces 100, as when worn, the element 20 assumes a generally hourglass shaped top plan view. The portion of the element 20 which lies beneath the pudendum of the wearer between the anterior commissure and the posterior commissure, when worn, is the central region 62. Therefore, when the preferred napkin 10 embodiment of the present invention is worn, the central region 62 of the element 20 shown in FIG. 12 extends from about the line 81 which is disposed beneath the wearer's anterior commissure to about the line 82 which is disposed beneath the wearer's posterior commissure. The distance between the lines 81 and 82 or their relative position on the napkin 10 can vary depending upon the size of the wearer and the positioning of the napkin 10. The portion of the element 20 extending forward from about the line 81 to the front end edge 32 is the front region 61. The portion of the element 20 extending backward from about the line 82 to the back end edge 32 is the back region 63. Note that when underpants are worn, the front region 61 and the back region 63 shown in FIG. 13 may be forced to curve upwards (not shown).

Figure 9:
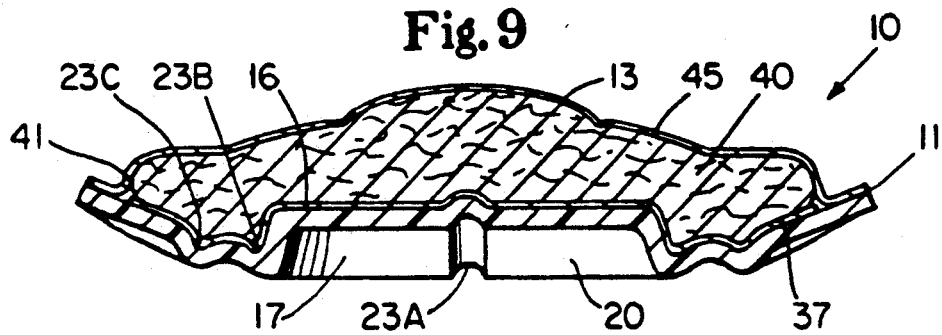
FIG. 9 is a lateral cross-sectional view of the preferred sanitary napkin embodiment shown in FIG. 1 taken along section line 9—9 of FIG. 1 through the portion of the sanitary napkin which is disposed beneath the center of the vaginal orifice when the sanitary napkin is worn.
Figure 16:
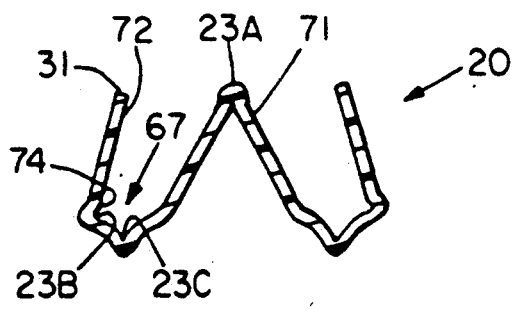
FIG. 16 is a lateral cross-sectional view of the preferred deformation element embodiment shown in FIG. 12 taken along section line 16—16 of FIG. 12 through the portion of the deformation element which is disposed beneath the center of the vaginal orifice when the preferred sanitary napkin embodiment of the present invention shown in FIG. 1 is worn.
Figure 17:
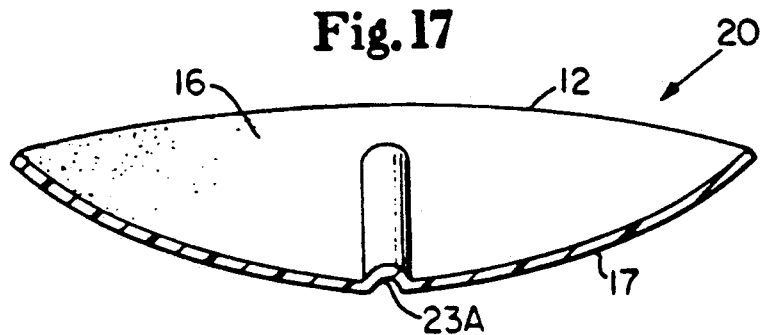
FIG. 17 is a lateral cross-sectional view of the preferred deformation element embodiment shown in FIG. 12 taken along section line 17—17 of FIG. 12.

When the preferred embodiment of the napkin 10 shown in FIGS. 1 through 5, is subjected to lateral compressive forces 100 when worn, the central region 62 of the element 20 can assume a number of different cross-sections ranging from its at-rest configuration shown by cross-section in FIG. 9 to the in-use configuration shown by cross-section in FIG. 16. As seen in FIG. 16, when the preferred sanitary napkin 10 is subjected to lateral compressive forces 100 when worn, the element 20 assumes a generally "W" shaped cross-section in the central region 62. As seen in FIG. 16, the walls 72 have assumed a substantially vertical position. The element side edges 31 remain adjacent to the walls 72, but are now displaced to a position above the walls 72 and into the uppermost part of the wearer's legs at the crotch where there is minimum movement and the least cause for irritation. The bases 74 of the walls 72 are adjacent to the thigh hinges 23B. The thigh hinges 23B are provided to allow the walls 72 to bend about the thigh hinges 23B, thereby assuming a substantially vertical position. Valleys 67 are formed above and around where the bases 74 of the walls 72 meet the thigh hinges 23B. The valleys 67 are particularly useful in diffusing exudates lengthwise to better utilize the total absorbent capacity of the napkin 10. From the thigh hinges 23B to the protuberance hinges 23C the element 20 slopes inwards and downwards. Between the protuberance hinges 23C, the body facing surface 16 of the element 20 has a convex upward configuration, and more particularly a generally inverted "U" shaped configuration. In addition, in the preferred embodiment shown in FIG. 16, the element 20, and particularly the protuberance 71 has a generally inverted "U" shaped cross-section. In the preferred embodiment, the convex upward configuration is generally symmetrically located between the longitudinal side edges 11, which in this embodiment are synonymous with the element side edges 31. The linear central hinge 23A is generally symmetrically located between the protuberance hinges 23C, along the longitudinal centerline 90 and along the apex of the convex upward configuration.

Before the body facing surface 16 of the element 20 can deform into the shape depicted in FIG. 16, the element's 20 upward movement may be impeded if the body surface 13 of the napkin 10 makes intimate contact with the wearer's pudendal region, and more specifically the external surfaces of the labia majora. If such occurs, the element 20, and specifically in a preferred embodiment the protuberance 71, will deform, and more particularly in a preferred embodiment, spread or bulge outwards. A comparison of FIGS. 16 and 20 illustrates how in a preferred embodiment the protuberance 71 deform when the protuberance's 71 upward movement is restricted by the external surfaces of the pudendal region.

Referring again to FIG. 12, it is seen that the major portion of the front region 61 is generally circular when viewed from above the body facing surface 16. The front region 61 remains generally circular because it is located beyond the thighs and is, therefore, not directly affected by the lateral compressive forces 100 which are exerted by the wearer's thighs. However, the region 61 is indirectly affected by the compressive forces 100 of the wearer's thighs and, in consequence thereof, assumes some anatomy conforming shapes. Generally, the front region 61 of the element 20 has an upwards opening cup shape when the napkin 10 is worn. This shape is depicted by cross-section in FIG. 17. The curved end edge 32 in the front region 61 along with the flexure hinges 23A, 23B, and 23C facilitate the formation of this cup shape.

Figure 18:
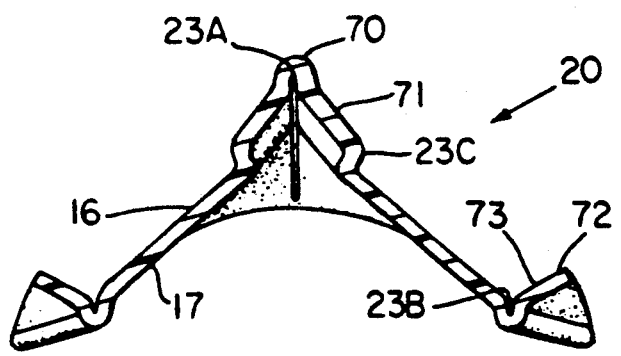
FIG. 18 is a lateral cross-sectional view of the preferred deformation element embodiment shown in FIG. 12 taken along section line 18—18 of FIG. 12.
Figure 19:
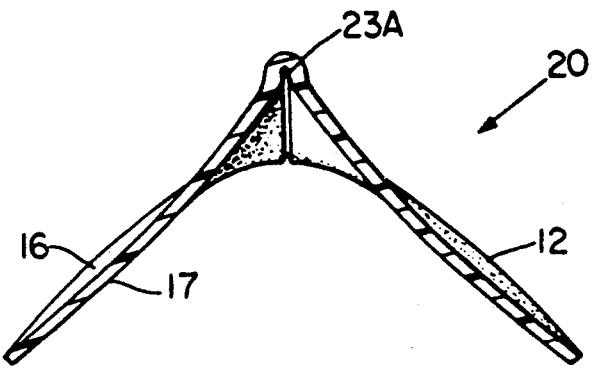
FIG. 19 is a lateral cross-sectional view of the preferred deformation element embodiment shown in FIG. 12 taken along section line 19—19 of FIG. 12.

In the preferred embodiment shown, the back region 63, like the front region 61, also assumes some anatomy conforming cross-sections when the napkin 10 is worn. However, in order to adapt to the different shapes of the anatomy in the buttocks region of the wearer, the cross-sections are very different from those in the front region 61. In a preferred embodiment, as shown in FIGS. 18 and 19, the back region 63 is configured to fit the gluteal groove of a wearer when the napkin 10 is worn. In the back region 63, the body facing surface 16 of the element 20 has a convex upward configuration. In the preferred embodiment, the back region 63 of the element 20 has a convex upward cross-section. The cross-section of the back region 63 best depicting this shape is shown in FIG. 18. As seen in the side view of the element 20 shown in FIG. 13 and in the cross-sections shown in FIGS. 18 and 19, the central hinge 23A, which is at the apex of the convex upward configuration in the central region 62, remains at the apex of the convex upward configuration into the back region 63. Since the napkin 10 will in all probability be worn with an undergarment, such as panties, the upward forces of the undergarment will preferably cause the back region 63 and the rearward part of the central region 62 to curve upwards and follow the curve of the buttocks. The body facing surface 16 of the element 20 in the back region 63 has a ridge 70 which is configured to fit the gluteal groove of the wearer, when worn. The ridge 70 is generally symmetrically located between the longitudinal side edges 11 of the napkin 10 along the longitudinal centerline 90. The ridge 70 fits the gluteal groove of the buttocks to provide stability against sideward shifting of the napkin 10. Because the depth of the gluteal groove varies as it moves from the anus towards the wearer's back, the back region 63 of the element 20 is designed so that it flattens out somewhat and the ridge 70 becomes less pronounced as the ridge 70 nears the end edge 12 of the back region 63. This change in formation is evidence by a comparison of FIG. 18, which is a cross-section through the back region 63, with FIG. 19, which is also a cross-section through the back region 63 but which is located more towards the end edge 12 of the back region 63.

Basically, without intending to limit the scope of the sanitary napkin 10 and particularly the deformation element 20 of the present invention as shown in FIGS. 1 through 13 and 16 through 20, the present invention is intended to function and provide the benefits as follows. The following is a description of only one means of progressive deformation of the napkin 10 and it should be recognized that other means are available. The napkin 10 is placed in the wearer'panties or directly adjacent to the wearer's crotch area so that the body surface 13 of the napkin 10 is facing and generally adjacent to the pudendal region. When the wearer brings her thighs together, compressive forces 100 are exerted on the longitudinal side edges 11, which in the preferred embodiment described and shown are synonymous with the element side edges 31, causing the element side edges 31 in the central region 62 to be forced inwards. This inward movement of the element side edges 31 consequently causes the walls 72 to bend about the thigh hinges 23B and thereby assume a substantially vertical position. As the napkin 10 is further compressed, the now substantially vertically standing walls 72 are displaced inwards towards the longitudinal axis 90. As the walls 72 are displaced inwards, the thigh hinges 23B, which are now at the base 74 of the walls 72, are also displaced inwards. Because the protuberance 71 is above the thigh hinges 23B, the thigh hinges 23B move beneath the protuberance 71, causing the protuberance 71 to flex while bending about the protuberance hinges 23C and the central hinge 23A. Thus, as seen in FIG. 16, the body facing surface 16 of the element 20, and particularly that portion of the body facing surface 16 which is superimposed over the protuberance 71, has a convex upward configuration, and more specifically, an inverted "U" shaped configuration. In addition, that portion of the body facing surface 16 having a convex upward configuration, in conjunction with the pudendal facing surface 73 of the walls 72, present a generally "W" shaped configuration. However, as mentioned previously, before the element 20 can assume the shape shown in FIG. 16, the body surface 13 of the napkin 10 may make intimate contact with the external surfaces of the pudendal region, thereby causing the element 20 and particularly the protuberance 71 to bulge outwards as shown in FIG. 20. Because the element 20 is flexure-resistant, the element 20 and particularly the protuberance 71 provides an outwardly directed biasing force against the downwardly distributed forces 500 of the wearer's pudendal region. Preferably, this biasing force creates a pressure promoted seal between the external surfaces of the labia majora and the body surface 13 of the napkin 10. Generally, enough lateral compressive forces 100 are provided by the wearer's thighs to put the body surface 13 of the napkin 10 in intimate contact with the external surfaces of the pudendal region, thereby causing the protuberance 71 of the element 20 to spread or bulge and create a biasing force which thereby seals the body surface 13 of the napkin 10 against the labia majora.

As the central region 62 is deforming, the front region 61 is simultaneously deforming into an upwards opening cup shape. The cup shaped front region 61 serves important functions. First, many women are concerned with the unobtrusiveness of their sanitary napkins when they are standing or laying on their backs since these are the positions when their forward groin area is most openly exposed. Coincidentally, these are also positions in which the wearer's thighs are exerting lateral compressive forces 100 on the napkin 10 and, in response thereto, the front region 61 of the element 20 is curving upwards. Therefore, rather than trying to remain flat and resist the forces of undergarments, the napkin 10 of the present invention is already curving upwards around the wearer's mons pubis and therefore cooperates with the forces of the undergarments so as to remain as unobtrusive as possible. Second, when an absorbent means 39 is placed in the front region 61 of the element 20 in such a way that the absorbent means 39 takes on the upward cupped-shape of the front region 61, certain other benefits are realized. For instance, it is likely that unabsorbed exudates will flow across the topsheet 45 and gravitate down along the convex upwards configuration to the front region 61. The cup-like shape of the front region 61, which preferably has its edge surface 12 in sealing engagement with the wearer's skin surfaces due to the upward pressure of the wearer's undergarments, provides an excellent retention area for the exudates until they can be absorbed by the absorbent means 39 or until the napkin 10 is discarded. In addition, the front region 61 may funnel the exudates back towards the valleys 67 in the central region 62, which is an area even less likely to cause soiling due to the protection provided by the vertically standing walls 72. Second, when a woman is lying on her stomach, menses may flow out of the vaginal orifice and along the surfaces of the labia minora where it may drip or continue to flow onto the mons pubis. The cup shape of the front region 61 forms a receiver which is ideal for catching and containing such drips and flows. Further, because the end edge 12 of the front region 61 is preferably in sealing engagement with the wearer's skin, any menses flowing along the skin will contact and be absorbed by, or at least contained by, the end edge 12 before it can leak beyond the end edge 12 of the napkin 10 and soil undergarments or linens.

While the central region 62 and the front region 61 are deforming, preferably the back region 63 is simultaneously deforming into some anatomy conforming configurations when the napkin 10 is worn, as shown in FIGS. 18 and 19. As the lateral compressive forces 100 of the thighs press inward against the walls 72 of the element 20, the back region 63 begins to bend downwards about the central hinge 23A, thereby assuming a convex upward configuration which is configured to fit between the buttocks of the wearer and in the gluteal groove. The forces of the buttocks on the napkin 10 on each side of the central hinge 23A, further facilitate the development of this convex upward configuration. Along the apex of the convex upward configuration of the element 20 runs a ridge 70 which is configured to fit the gluteal groove of the wearer. The ridge 70 provides stability against sideward shifting of the napkin 10. The ridge 70 also serves another important function. When a woman lies on her back, as when sleeping, some of the menses may not be deposited directly from the vaginal orifice onto the napkin 10. Instead, the menses may gravitate towards the posterior commissure of the vestibule, following these skin surfaces into the perineal groove, across and around the anus, and into the gluteal groove and the surrounding surfaces of the buttocks where it can soil undergarments and other linens. However, the element 20 of the present invention, and especially the back region 63, is designed such that the ridge 70, or an absorbent means 39 which might be superimposed over the ridge 70, will preferably be within the gluteal groove, preferably in contact with the wearer's skin surfaces so that any menses flowing along these skin surfaces will contact the ridge 70, or an absorbent means 39 which is superimposed over the ridge 70, and be absorbed into it before coming in contact with undergarments or other linens.

The self-conforming characteristics of the sanitary napkin 10 of the present invention render unnecessary a requirement for independent attaching means for the napkin 10 for some wearers and for some embodiments. The slight biasing force provided by the wearer's undergarments coupled with the outwards biasing force of the element 20 against the wearer's thighs will establish a sufficient means for maintaining the sanitary napkin 10 in the desired position. Ideally, attachment directly to the undergarment or body is not required, recognizing that such attachment may under some circumstances override the more preferred direct association of the napkin 10 solely with the wearer's body; the wearer then facing the possibility that movement of the undergarment relative to the pudendum will translate into some motion within the napkin 10 itself. However, there may be situations where it is desirable to provide some ancillary attaching means. Accordingly, there may optionally be provided an adhesive member for securing the napkin 10 to the undergarments of the wearer. This adhesive member is most preferably a conventional pressure sensitive adhesive bearing a release paper which may be removed to expose the adhesive for purposes of attachment to an undergarment. In this manner, the wearer may exercise the option of attaching the napkin 10 or not as a matter of individual preference. It is noteworthy that even in those instances where the option to secure the napkin 10 to the undergarment is elected, a comparatively small amount of adhesive in a few locations or zones is most preferably provided as opposed to more conventional longitudinal, multiple strips or the like. Because the napkin 10 of the present invention assumes a number of cross-sections along its longitudinal length which are very different from the original configuration of the napkin 10, it is advantageous when determining where to place adhesive to find points on the garment surface 14 of the napkin 10 which retain their relative position with respect to the wearer's undergarment, when worn. Preferred locations for attachment of adhesive for the napkin 10 shown in FIGS. 1 through 5 are on the bottom surface 17 of the element 20 along a short central length of the thigh hinges 23B and/or an oval patch across the ends of the central hinge 23A near each of the ends 32 of the napkin 10. This approach provides a generally acceptable compromise for those who wish the security of attachment of the napkin 10 to the undergarment while those points of attachment are selected as the least influential relative to the potential contribution to rubbing or chafing occasioned by relative motion between the undergarment (and attached napkin) and the wearer's pudendum.

A number of alternative embodiments of the napkin 10, and more specifically the element 20 and the flexure means 23, are contemplated within the foregoing description. For example, in an alternatively preferred embodiment of the present invention, the deformation element 20 is reformable. As used herein, the term "reformable" refers to the ability of an element to return substantially to a configuration the element held prior to the influence of certain external forces. The element may reform because of the influence of other external forces and/or because of the physical properties of the material of which the element is comprised.

In another alternatively preferred embodiment of the present invention, the deformation element 20 is resilient. As used herein, the term "resilient" refers to an element which after the removal of external forces will return substantially to a configuration the element held prior to the influence of external forces, solely because of the physical properties of the material of which the element is comprised. An example will help clarify and differentiate the terms "reformable" and "resilient." Imagine a flat, rectangular shaped object. Now imagine that the object is squeezed from the sides so that its sides are displaced inwards towards each other and its middle bulges up. Now imagine that the squeezing forces are relieved. If the object returns substantially to its original flat, rectangular shape, then the object is resilient. If the object returns substantially to its original flat, rectangular shape only after the influence of some other external force, such as by pressing down on the bulge, then the object is reformable, but not resilient. Thus, a resilient element is necessarily reformable but a reformable element may not be resilient. When a preferred embodiment of the sanitary napkin 10 of the present invention is worn, the external forces which render the deformation element 20 reformable are the lateral compressive forces 100 of the wearer's thighs, the downwardly distributed forces 500 of the wearer's pudendum, the forces of the wearer's panties and possibly other external forces which act upon the napkin 10 from, for example, a chair or bed when the wearer sits or lays. As mentioned earlier, in preferred embodiments of the napkin 10, the absorbent means 39, and specifically the absorbent core 40 and the topsheet 45, flex generally in cooperation with the deformation element 20. Thus, when the thighs of a wearer apply lateral compressive forces 100 to the deformation element 20 causing it to bend and flex in the regions 61, 62 and 63 as previously described, the absorbent means 39 generally mimics such deformations. As the lateral compressive forces 100 are lessened or relieved, such as when the wearer's thighs are spread, the reformable or resilient nature of the deformation element 20 is realized and the deformation element 20 begins to reform substantially to the shape the element 20 had prior to the influence of the external lateral compressive forces 100. Likewise, in cooperation with the reformation of the element 20, the absorbent means 39 preferably reforms to the shape the absorbent means 39 had prior to the influence of external forces. In preferred embodiments, as the wearer moves while walking, crossing her legs, squatting, etc., external forces which are being exerted on and relieved from the napkin 10 cause the napkin 10 as a whole, and the deformation element 20 and the absorbent means 39 individually, to go through a multitude of deformations and reformations.

In another alternatively preferred embodiment of the element 20 (not shown), the body facing surface 16 of the element 20 does not have a preformed convex upward configuration like the preferred element 20 described earlier and illustrated in FIGS. 6 through 8, but instead is planar across its width or has a concave downward configuration. In such embodiments, the body facing surface 16 must assume a convex upward configuration after the application of lateral compressive forces 100 to the longitudinal side edges 11 of the napkin 10 by the wearer's thighs.

Another alternative embodiment of the sanitary napkin 10 of the present invention is shown in FIGS. 21 and 22. As shown in FIGS. 21 and 22, the deformation element 20 is disposed between a liquid pervious topsheet 45 and an absorbent core 40. A liquid impervious barrier sheet 55, as is well known in the art, is provided adjacent to the second major surface 44 of the absorbent core 40 so as to prevent the exudates absorbed and contained in the absorbent core 40 from soiling articles such as bedsheets and undergarments which contact the napkin 10. The barrier sheet 55 extends slightly beyond the core end edges 42 and is folded about halfway up the core side edges 41 to prevent leakage. The absorbent core 40 is superimposed onto an adhesive which is applied to the inner surface of the barrier sheet 55 and which is intended to hold the barrier sheet 55 in place on the absorbent core 40. In this embodiment, the topsheet 45 extends around the side edges 41 of the absorbent core 40 and over the barrier sheet 55 where it overlaps itself on the garment surface 14 of the napkin 10 so as to completely envelope the element 20, the absorbent core 40, and the barrier sheet 55, thereby forming what is commonly known as a "tubular napkin". The overlapping portions of the topsheet 45 are adhered to each other along the garment surface 14 of the napkin 10 and the end edges of the topsheet 45 and the barrier sheet 55 are heat-sealed to each other to form the end edges 12 of the napkin 10.

In this embodiment, the element 20 comprises wood pulp fibers which have been compressed into a semi-rigid paper-board-like sheet and suitably bonded so as to be moisture stable. Alternatively, the element 20 could be comprised of many of the materials previously described. Because this element 20 has a greater flexure-resistance than the element 20 previously described and because it is smaller and has fewer flexure means 23, and particularly fewer flexure hinges, than the element 20 previously described, it is somewhat less body conforming than the previous element 20. The flexure means 23 is a longitudinal flexure hinge which, in this embodiment, is simply a longitudinal set 23E to the element 20 (i.e., a preferential fold or crease, scoring, embossing or indenting) along the longitudinal axis 90, which tends to pitch the element 20 upwardly along the fold, thus causing the element 20 to assume a somewhat flattened, inverted "V" shaped cross-section having a ridge 70, as shown in FIG. 22. The element 20 is placed in the napkin 10 in this configuration so that when the napkin 10 is worn, the element 20 will fold in a controlled and predetermined manner such that the body facing surface 16 of the element 20 will have a convex upward configuration. The lateral compressive forces 100 of the wearer's thighs may be applied to the element side edges 31 directly or they may be applied indirectly by transmission of the forces 100 from the longitudinal side edges 11 of the napkin 10 through other members of the napkin 10. When worn, the lateral compressive forces 100 of the thighs cause the element 20 to assume a more defined, inverted "V" shaped cross-section. In the preferred embodiment, the element 20 has a generally hourglass shape. While other shapes such as rectangular, square, oval, and others are effective and acceptable, it is believed that the hourglass shape offers unique benefits, when worn, in that the inwardly curved middle portion will accommodate the wearer's thighs while the wider end portions, which resultingly have a greater surface area for acquisition of menses and a greater cross-sectional absorptive capacity than the thinner middle portion, are positioned so that when worn the forward end portion will be aligned with and be beneath the vaginal orifice. In the preferred embodiment, the element 20 has a thickness of about 2.0 millimeters, a length along the longitudinal axis 90 of about 19.0 centimeters, a width across the ends of about 6.5 centimeters and a width across the lateral axis 80 of about 4.0 centimeters.

Figure 23:
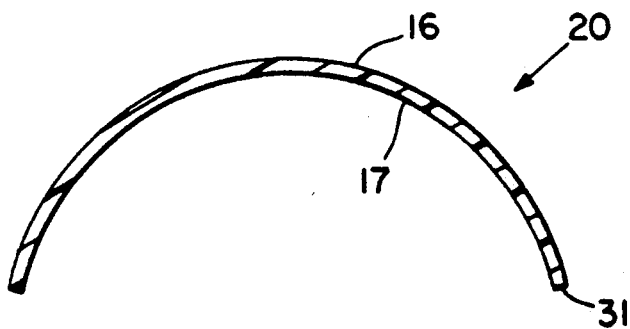
FIG. 23 is a lateral cross-sectional view of another alternatively preferred deformation element embodiment of another alternatively preferred sanitary napkin embodiment of the present invention taken through the portion of the deformation element which is disposed beneath the center of the vaginal orifice when the sanitary napkin is worn.

Another alternatively preferred embodiment of an element 20 is shown in FIG. 23. As with the element 20 shown in FIGS. 6 through 8, this element 20 is preferably comprised of a foam material and is flexure-resistant, reformable and resilient. The element 20 in its at rest configuration has a convex upward configuration. The flexure means 23 of the element 20 is inherent in the element 20 simply due to its preformed arcuate shape. Thus, when lateral compressive forces 100 are applied to the element side edges 31, the element 20 simply maintains a convex upward configuration as it flexes. As previously described, the element 20 is preferably overlayed by an absorbent core 40 and a topsheet 45, which are superimposed on the element 20.

Figure 24:
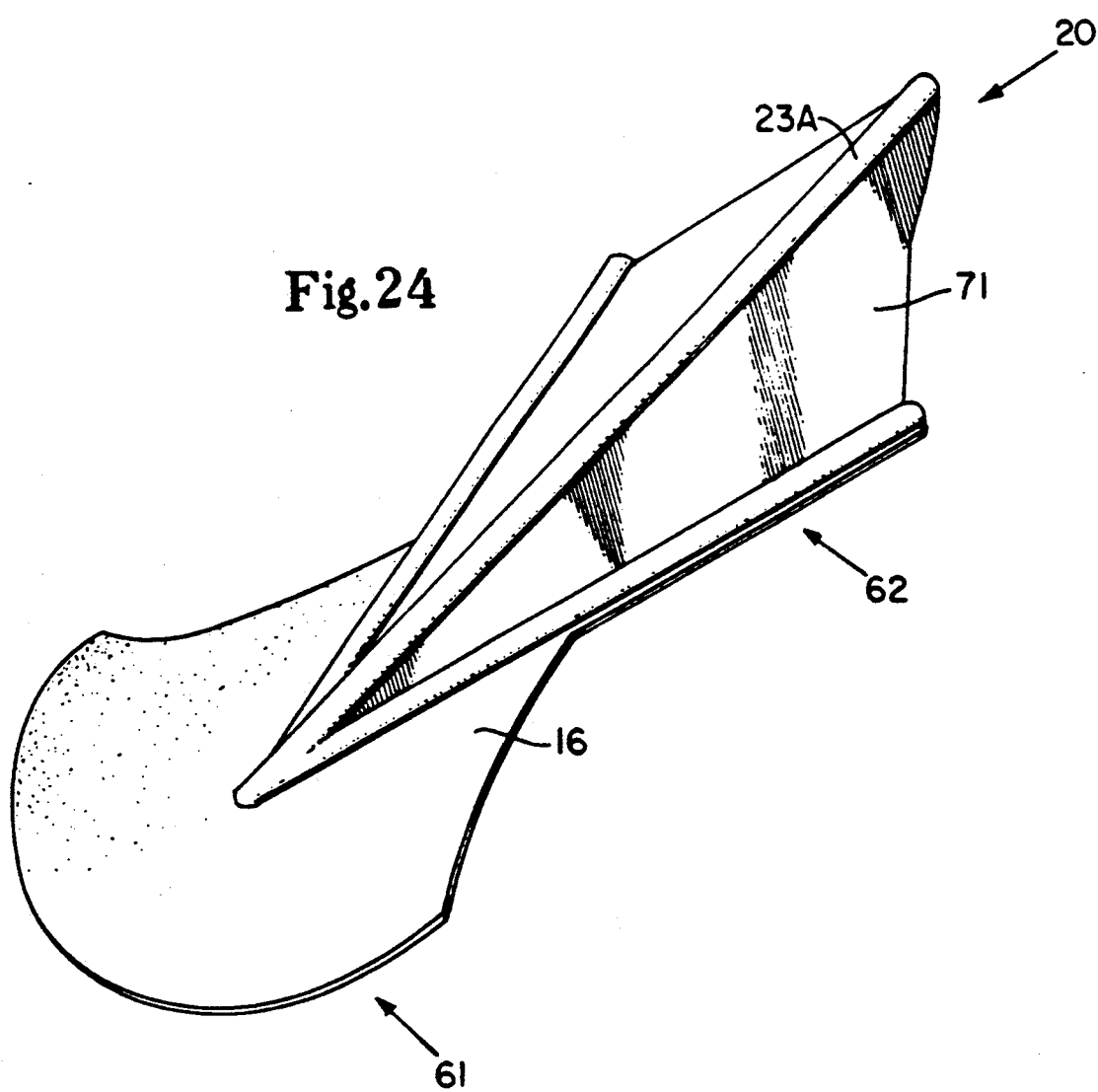
FIG. 24 is a top perspective view of another alternatively preferred deformation element embodiment of another alternatively preferred sanitary napkin embodiment of the present invention.

Another alternatively preferred embodiment of a deformation element 20 of the present invention is shown in FIG. 24. The deformation element 20, as shown, is comprised of a foam as previously described. The deformation element 20 has a pre-formed inverted "U" shape in the central region 62 and a pre-formed upward conical shape in the front region 61. In this embodiment, the flexure means 23 is a longitudinally extending linear central hinge 23A having a generally inverted "U" shaped cross-section. The element 20 acts much like the element 20 shown in FIGS. 6 through 8 under lateral compressive forces 100, the main differences being that the element 20 in this alternatively preferred embodiment has a greater degree of pre-formed shape and also, this element 20 is not symmetrical in the longitudinal direction and would, therefore, have to be consciously positioned on the wearer so that it was aligned in the proper direction. Further, this element 20 is not intended to be a liquid impermeable backing member for the napkin 10. Instead, the element 20 has an hourglass shaped absorbent core 40 placed on its body facing surface 16 and a liquid impervious barrier sheet 55 covering its bottom surface 17 and extending beyond its side edges 31 and end edges 32 (not shown). The absorbent core 40 is covered by a liquid pervious topsheet 45 which extends beyond the edges of the absorbent core 40 and the element 20 where it is affixed to the barrier sheet 55 (not shown).

In still another alternative embodiment of the present invention (not shown), the deformation element 20 is isolated from contact with moisture. Thus, such an embodiment might comprise from the body surface 13 down a liquid permeable topsheet 45, an absorbent core 40, a liquid impermeable barrier sheet 55, a deformation element 20, and another liquid impermeable barrier sheet 65, the sheets 45, 55 and 65 being sealed about their peripheries. In such an embodiment, the deformation element 20 is not susceptible to being wetted when worn and thus, the deformation element 20 may be comprises of moisture unstable materials such as compressed, unbonded fluff pulp.

Figure 25:
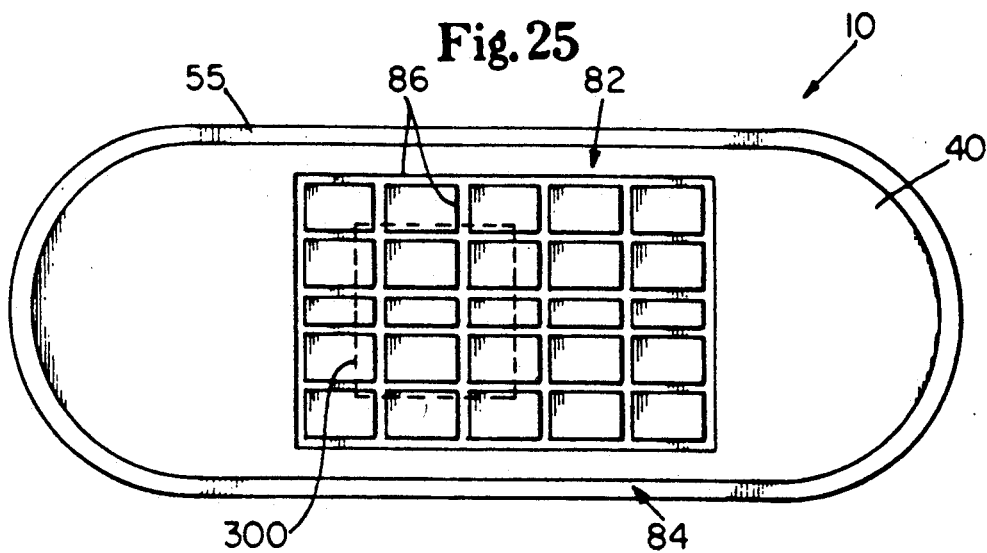
FIG. 25 is a top plan view of another alternatively preferred deformation element embodiment and sanitary napkin embodiment of the present invention, the topsheet not being shown.

Yet another alternatively preferred embodiment of a sanitary napkin 10 and specifically a deformation element 20 of the present invention is shown in FIG. 25. The napkin 10 comprises a barrier sheet 55, an absorbent core 40 and a topsheet 45 (not shown). The absorbent core 40 is comprised of fluff pulp. In a middle portion 84 of the absorbent core 40 the fluff pulp is embossed in a lattice pattern 82 such that the lattice members 86 are highly densified. Further, because the absorbent core 40 is susceptible to wetting, the fluff pulp is adhesively bonded throughout the middle portion 84 by a water insoluble adhesive. Thus, the deformation element 20 of the present invention is said to be the middle portion 84 of the absorbent core 40. The fluff pulp can be bonded or unbonded beyond the middle portion 84. The absorbent core 40 has a preferential set (not shown) on its second major surface 44 along the longitudinal axis 90 so that the deformation element 20 is inclined to have a convex upward configuration when the sanitary napkin 10 is worn. The absorbent core 40 is about 20.5 centimeters long, about 13.0 centimeters wide, about 1.0 centimeters thick in the unembossed areas and about 0.5 centimeters thick in the embossed areas. The middle embossed portion 84 of the absorbent core 40 is about 10.0 centimeters long and about 6.3 centimeters wide. The embossed lattice members 86 are about 3.0 millimeters wide. For illustration, if the Circular Bend Procedure were to be performed on this element 20, a likely 37.5 by 37.5 millimeter test sample might be that portion of the element 20 enclosed by the square 300, as shown by dashed lines in FIG. 26. Of course, a person would want to test a number of other portions also but this portion would seem to be the most flexure-resistant since this portion has as great a proportion of densified area as any other portion of the element 20. It should be noted that the test specimens would need to be tested using the large diameter test plate since the specimens would have an uncompressed optical caliper greater than 6.35 millimeters.

Figure 26:
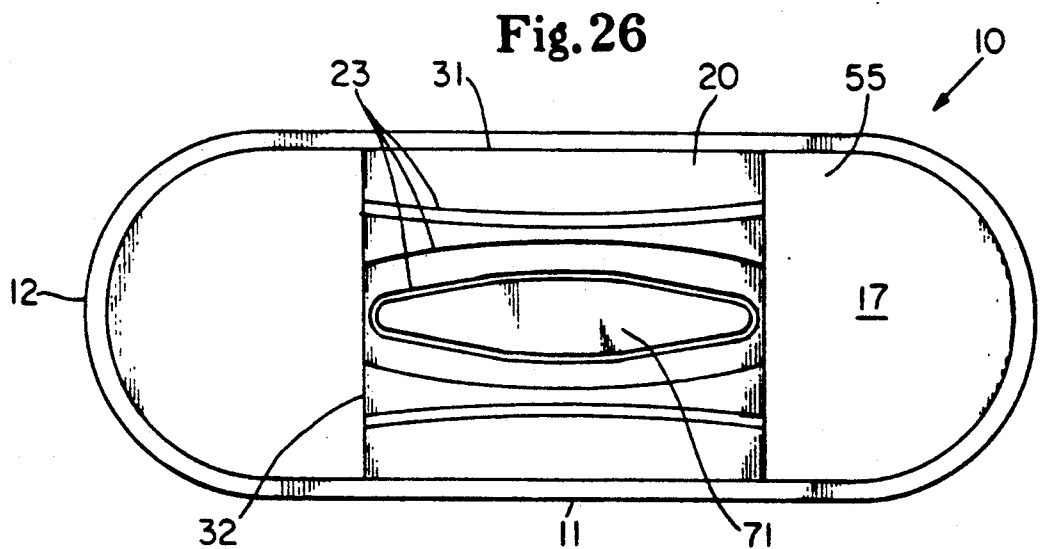
FIG. 26 is a bottom plan view of another alternatively preferred deformation element embodiment and sanitary napkin embodiment of the present invention.
Figure 27:
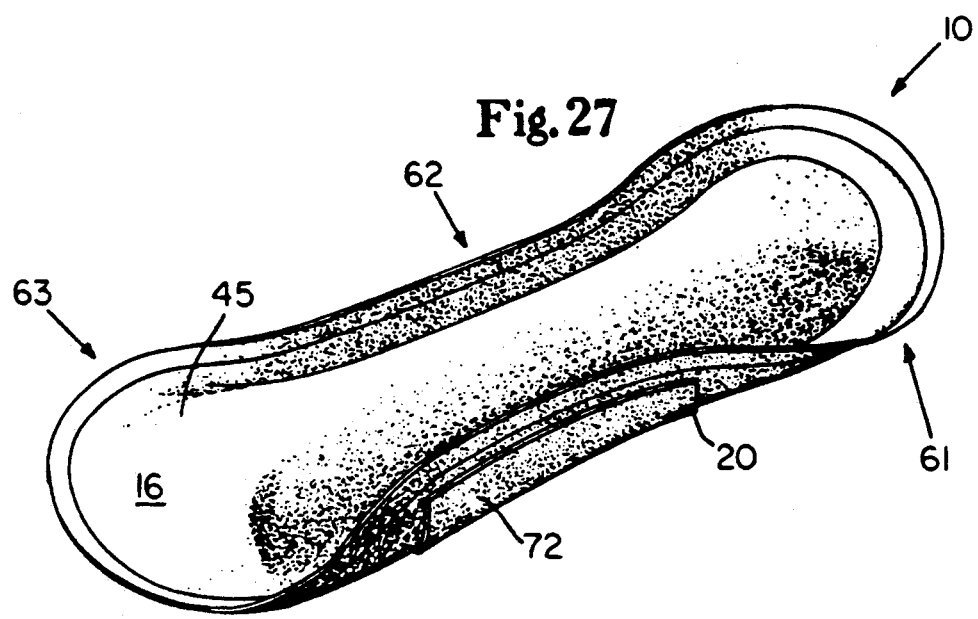
FIG. 27 is a top perspective view of the alternatively preferred deformation element embodiment and sanitary napkin embodiment shown in FIG. 26 as it would appear when worn.

Still another alternative embodiment of a sanitary napkin 10 of the present invention is shown in FIGS. 26 and 27. In this embodiment, the sanitary napkin 10 comprises, from the body surface 13 down, a topsheet 45, a wipe acquisition sheet 93, a tissue layer 94, an absorbent core 40, a barrier sheet 55, and a deformation element 20. As seen in FIG. 26, in this embodiment the deformation element 20 is centered in the napkin 10. Basically, the deformation element 20 of this embodiment is generally similar to the midportion of the deformation element 20 shown in FIGS. 6 and 7. In this embodiment, the deformation element 20 is affixed to the garment facing surface of the barrier sheet 55. However, the deformation element 20 might be disposed in a number of positions throughout the laminates of the napkin 10, such as between the absorbent core 40 and the barrier sheet 55. Beyond the ends 32 of the deformation element 20, the sanitary napkin 10 is highly flexible. Further, the napkin 10 has a relatively very thin caliper, especially beyond the ends 32 of the element 20. In a preferred embodiment, the topsheet 25 is an apertured formed film, the wipe acquisition sheet 93 is an apertured nonwoven sheet, such as the SONTARA 8407, manufactured by E. I. DuPont Nemours & Company of Wilmington, Del., (SONTARA Registered Trademark by E. I. DuPont Demours & Company), the tissue layer 31 is a wet-laid tissue such as that disclosed in U.S. Pat. No. 3,301,746; entitled "Process For Forming Absorbent Paper By Imprinting A Fabric Knuckle Pattern Thereon Prior To Drying And Paper Thereof", which patent issued to Sanford and Sisson on Jan. 31, 1967, and the absorbent core 40 is a superabsorbent laminate such as the WATER-LOCK L-535 available from the Grain Processing Corporation of Muscatine, Iowa (WATER-LOCK Registered Trademark by Grain Processing Corporation).

As seen in FIG. 27, the napkin 10, when subjected to the forces of the wearer's body, when worn, takes on a number of the beneficial shapes of the napkins 10 previously described. This embodiment is particularly useful for the following reason. The deformation element 20, and the areas of the napkin 10 superimposed over the element 20, take on a convex upward configuration beneath the vestibule and specifically beneath the vaginal orifice. Thus, the napkin 10 is able to acquire menses immediately as it exits the vestibule. In addition, beyond the ends 32 of the element 20, the napkin 10 is highly flexible and very thin. Thus, the napkin 10 is extremely comfortable, has a low wearing awareness, and conforms very nicely to the mons pubis and the gluteal groove.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. An externally worn disposable absorbent article comprising:
   a liquid pervious topsheet;
   a liquid impervious backsheet joined with said topsheet;
   an absorbent element disposed between said topsheet and said backsheet; and
   a moisture stable, flexure-resistant deformation element, said deformation element comprising a thermomoldable substance, said deformation element having a flexure means for inducing bending of said deformation element in a preconceived way into a preconceived convex upward cross section when the absorbent article is subjected to lateral compressive forces, said flexure means comprising a flexure hinge creating a different bend-resistance across the width of said deformation element, said hinge being thermomolded into said deformation element, said deformation element being joined to and vertically registered with said absorbent element.

2. The absorbent article of claim 1 wherein the absorbent article has a central region, a front region adjacent to and forward of said central region, and a back region adjacent to and backward of said central region, said flexure means being positioned in said central region.

3. The absorbent article of claim 2 wherein said back region is flexible.

4. The absorbent article of claim 3 wherein said flexure means comprises a pair of thigh hinges extending generally longitudinally along said deformation element.

5. The absorbent article of claim 4 wherein said flexure means additionally comprises a pair of protuberance hinges.

6. The absorbent article of claim 5 wherein said thigh hinges are each arcuate such that the longitudinal midpoint of the arc is the greatest distance from the side edges of said deformation element, and wherein said protuberance hinges are arcuate such that the longitudinal midpoint of the arc is the greatest distance from the longitudinal axis of said deformation element.

7. The absorbent article of claim 6 wherein said deformation element is superimposed on said absorbent element such that said deformation element is disposed between said topsheet and said absorbent element.

8. The absorbent article of claim 6 wherein said absorbent element is superimposed on said deformation element such that said deformation element is disposed between said absorbent element and said barrier layer.

9. The absorbent article of claim 1, 2, or 5 wherein said thermomoldable substance is selected from the group consisting of polyethylene, polypropylene, polyester, polybutylene, polyurethane, ethylene vinyl acetate, thermobondable cellulose, latex, silicone elastomerics or a combination thereof.

10. The absorbent article of claim 9 wherein said thermobondable substance is a thermobondable cellulose.

11. The absorbent article of claim 10 wherein said thermobondable cellulose comprises synthetic fibers blended with wood pulp.

* * * * *

UNITED STATES PATENT AND TRADEMARK OFFICE
CERTIFICATE OF CORRECTION

PATENT NO. : 5,300,055
DATED : April 5, 1994
INVENTOR(S) : KENNETH B. BUELL

It is certified that error appears in the above-identified patent and that said Letters Patent is hereby corrected as shown below:

Column 1, line 63, "Built-in" should read --Built-In--.

Column 7, line 50, "women" should read --woman--.

Column 13, line 61, "pudental" should read --pudendal--.

Column 16, line 9, "infection" should read --inflection--.

Column 16, line 53, "the generally" should read --generally--.

Column 18, line 9, "deform" should read --deforms--.

Column 19, line 11, "wearer'panties" should read --wearer's panties--.

Column 24, line 62, "comprises" should read --comprised--.

Signed and Sealed this

Eighteenth Day of June, 1996

BRUCE LEHMAN

Attest:

Attesting Officer

Commissioner of Patents and Trademarks